US006218370B1

(12) United States Patent
Bischoff et al.

(10) Patent No.: US 6,218,370 B1
(45) Date of Patent: Apr. 17, 2001

(54) GLYCEROLIPIDIC COMPOUNDS USED FOR THE TRANSFER OF AN ACTIVE SUBSTANCE INTO A TARGET CELL

(75) Inventors: Rainer Bischoff, Barseback (SE); Denis Heissler, Eckbolsheim; Abdesslame Nazih, Strasbourg, both of (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/171,129

(22) PCT Filed: Feb. 10, 1998

(86) PCT No.: PCT/FR98/00250

§ 371 Date: Oct. 13, 1998

§ 102(e) Date: Oct. 13, 1998

(87) PCT Pub. No.: WO98/34910

PCT Pub. Date: Aug. 13, 1998

(30) Foreign Application Priority Data

Feb. 10, 1997 (FR) .................................................. 97 01475
Dec. 12, 1997 (FR) .................................................. 97 15805

(51) Int. Cl.$^7$ .......................... A61K 9/127; A61K 31/70; C07H 21/02; C07H 21/04; C12Q 1/68; C12N 5/00
(52) U.S. Cl. ............................... 514/44; 536/23.1; 435/6; 435/325; 435/375; 424/450
(58) Field of Search ........................... 435/6, 320.1, 325, 435/375; 424/450, 1.11, 9.1, 9.341; 514/44, 2, 7; 536/23.1; 560/224; 530/323

(56) References Cited

U.S. PATENT DOCUMENTS 6,020,317 * 2/2000 Junichi et al. ....................... 514/44

FOREIGN PATENT DOCUMENTS

| 195 21 412 | 12/1996 | (DE) . |
| 0 685 234 | 2/1994 | (EP) . |
| 0 685 457 | 2/1995 | (EP) . |
| 94/05624 | 3/1994 | (WO) . |
| WO 94/19314 | * 9/1994 | (WO) . |
| WO 97/00214 | * 1/1997 | (WO) . |

* cited by examiner

Primary Examiner—John L. LeGuyader
Assistant Examiner—Janet Epps
(74) Attorney, Agent, or Firm—Burns, Doane, Swecker & Mathis, L.L.P.

(57) ABSTRACT

The invention concerns novel of compounds of formula (I) in which: $R_1$ and $R_2$, identical or different are $C_6$–$C_{23}$ alkyl or alkenyl radicals, linear or branched or —C(=O)-($C_6$–$C_{23}$) alkyl or —C(=O)-($C_6$–$C_{23}$) alkenyl, linear or branched, X is the oxygen atom or an amino —$NR_3$ radical, $R_3$ being a hydrogen atom or an inferior alkyl radical of 1 to 4 carbon atoms; n is a positive whole number from 1 to 6; m is a positive whole number from 1 to 6, and when n>1, m can be identical or different. The invention also concerns novel compositions of said compounds and of active substances in particular therapeutically, comprising at least a negative charge for inserting said active substances in cells. It concerns in particular novel complexes, of which the active substance consists of one or several nucleic acids, useful for cell transfection.

31 Claims, 10 Drawing Sheets

Figure 2A:
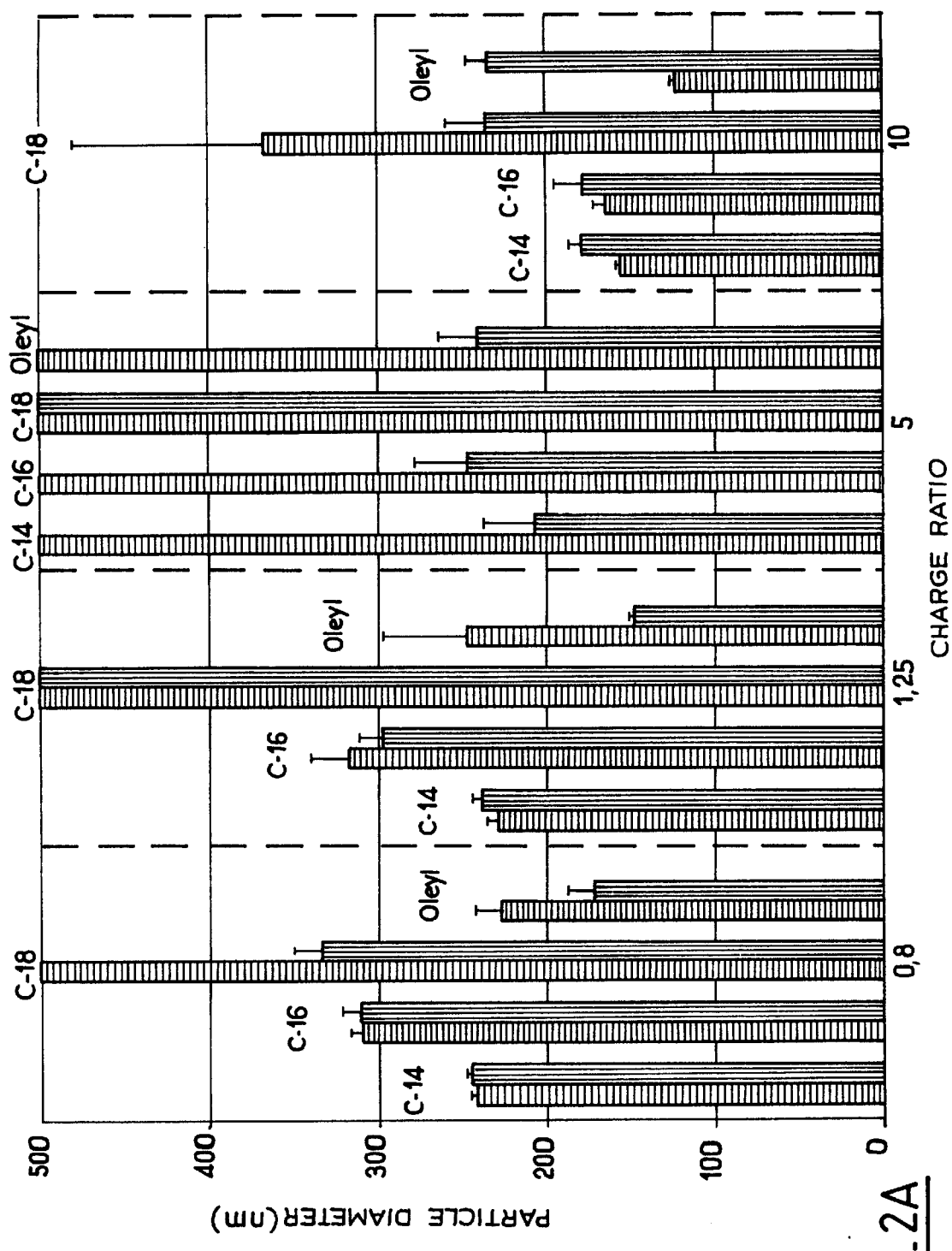

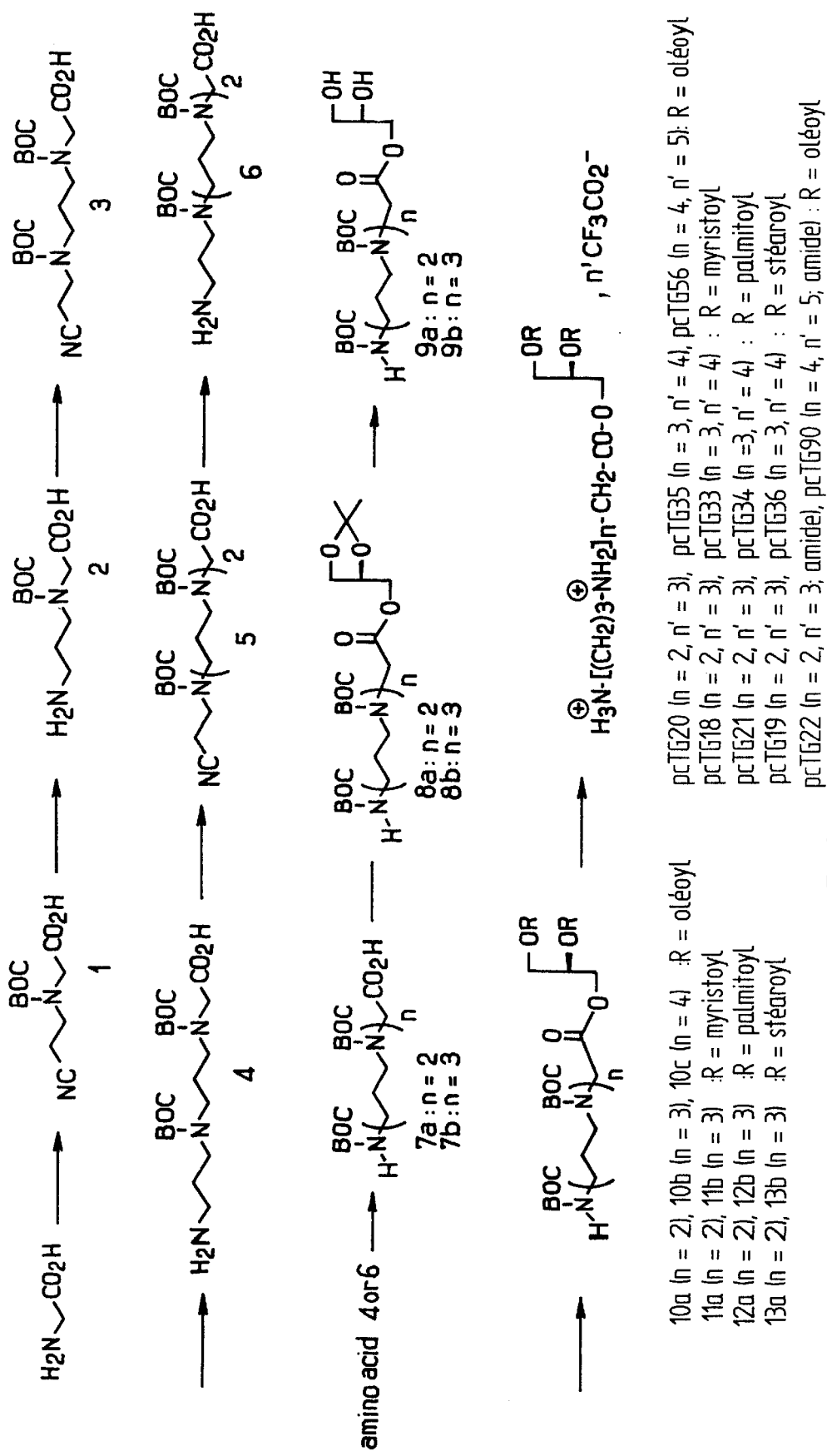
FIG_1

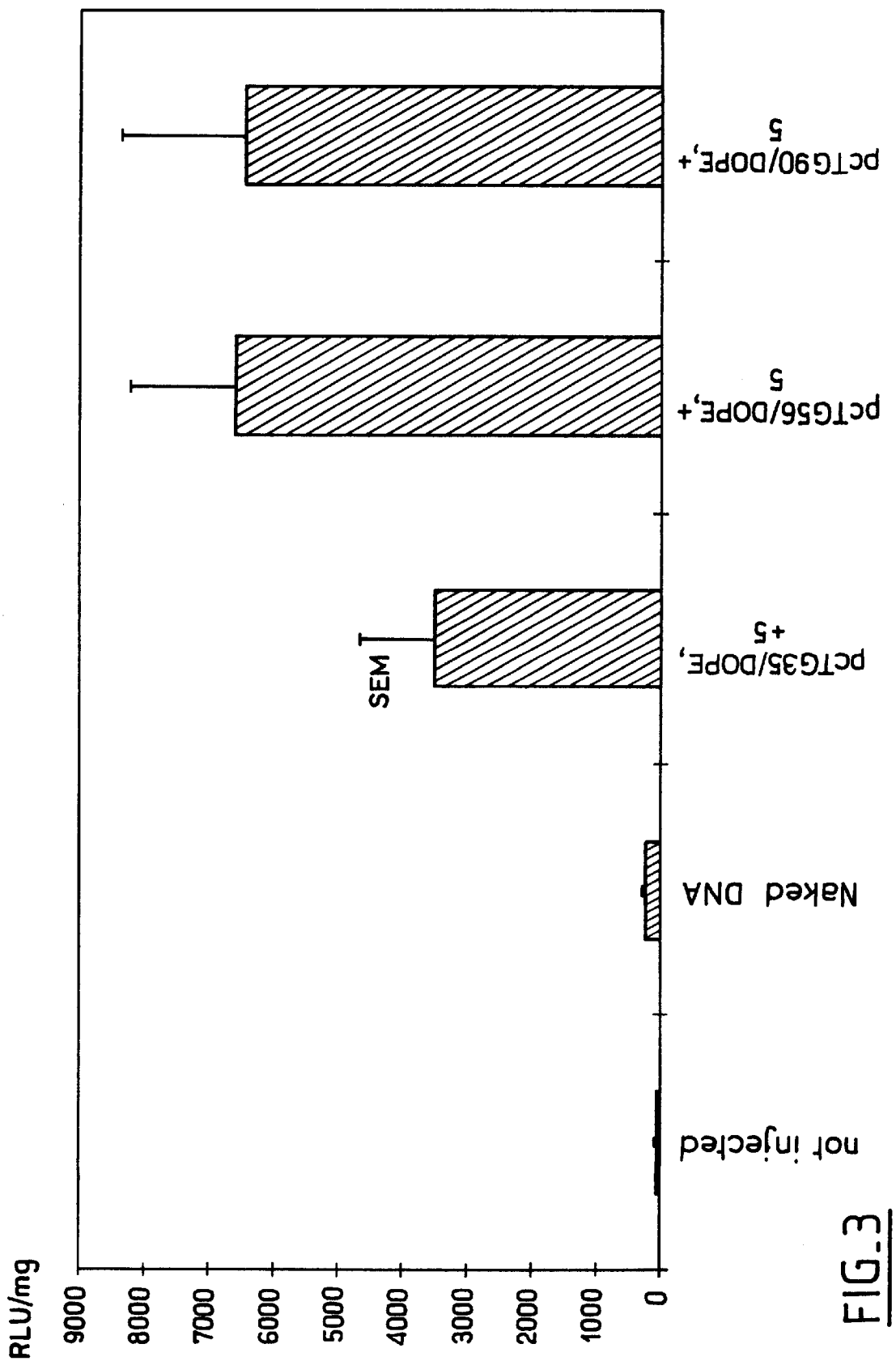
FIG._3

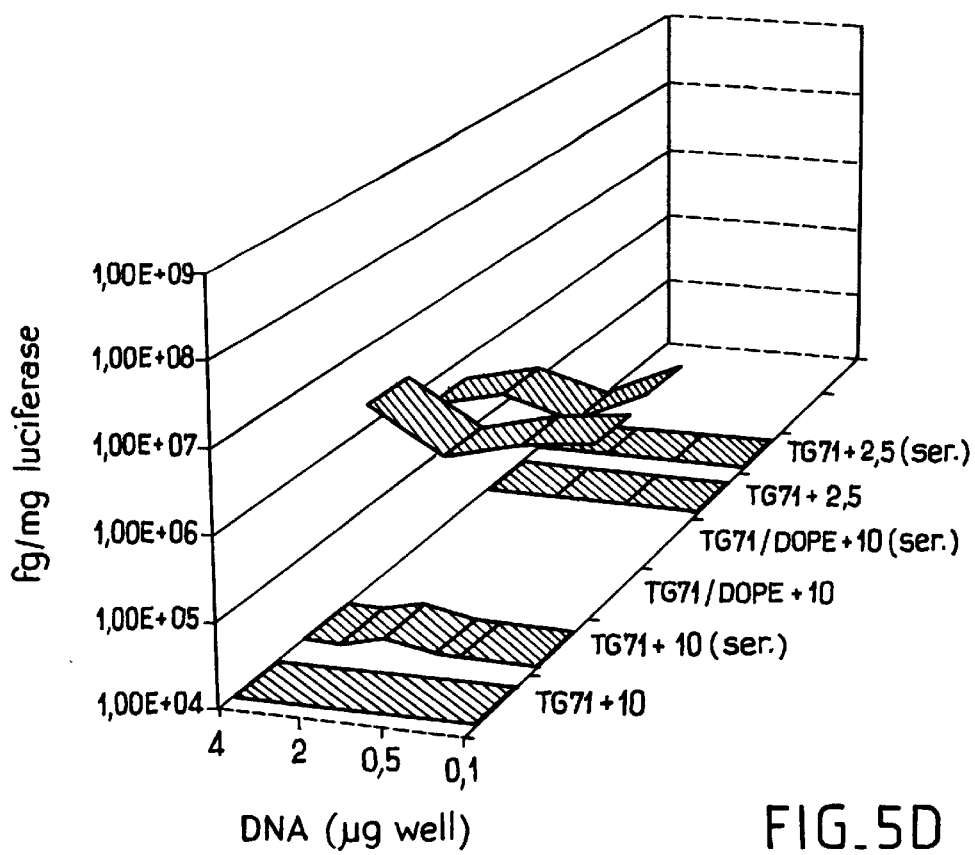
FIG_5D
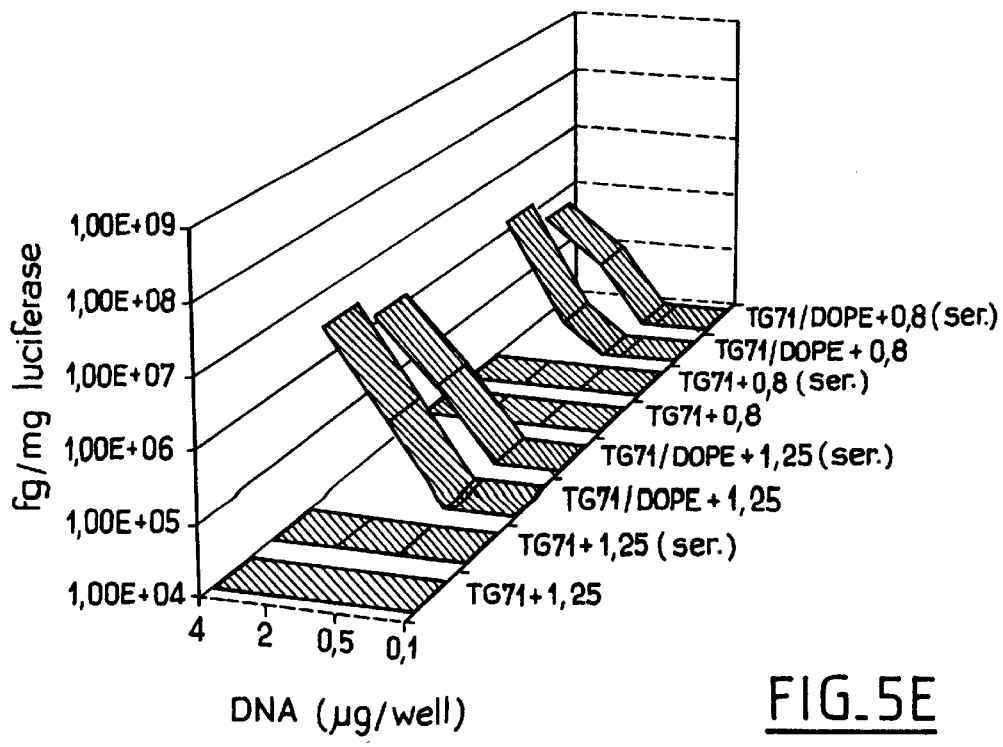
FIG_5E

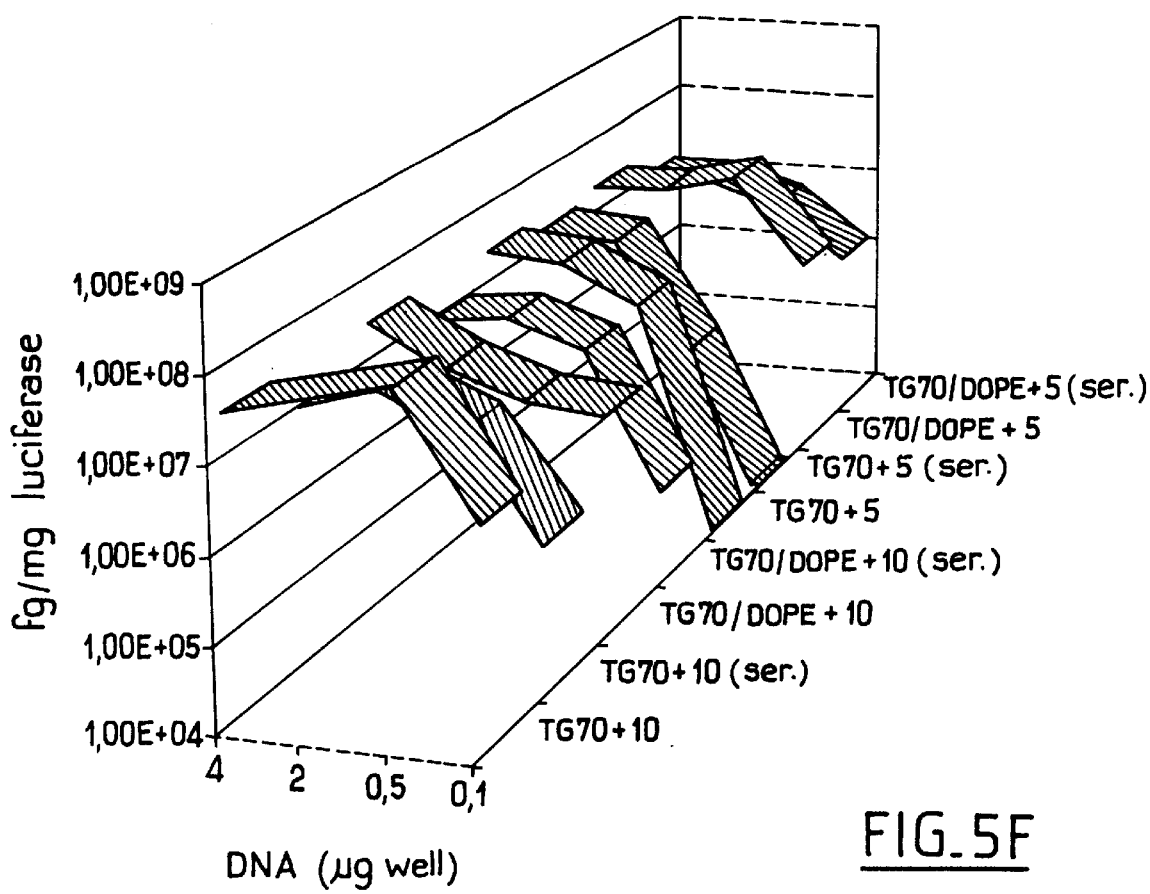
FIG._5F
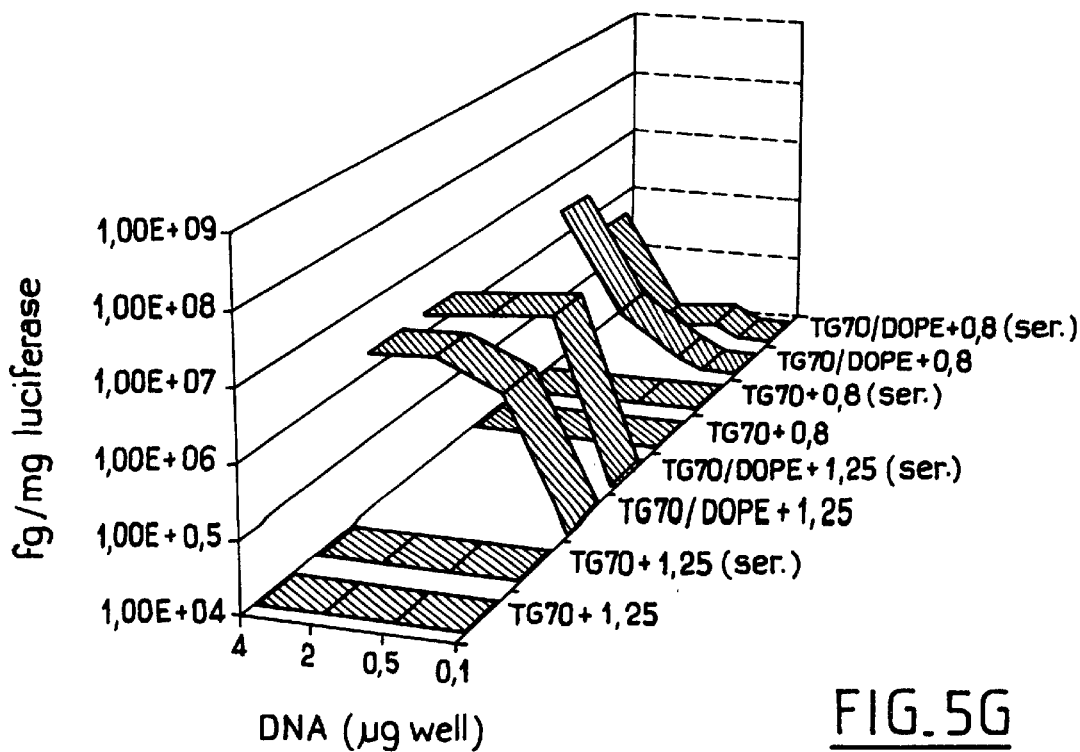
FIG._5G

GLYCEROLIPIDIC COMPOUNDS USED FOR THE TRANSFER OF AN ACTIVE SUBSTANCE INTO A TARGET CELL

The present invention relates to new glycero-lipid compounds and new compositions containing them. More particularly, the present invention relates to the use of said compounds or of said compositions to prepare a vector for transferring an active substance, in particular a therapeutically active substance comprising negative charges, in particular a polynucleotide, into a target cell, particularly a vertebrate cell, and more particularly a mammalian cell.

The transfer of a gene into a given cell is the very basis of gene therapy. This new technology, whose field of application is vast, makes it possible to envisage the treatment of serious diseases for which the conventional therapeutic alternatives are not very effective, or are even inexistent, and applies to diseases which are either of genetic origin (hemophilia, cystic fibrosis, myopathy and the like) or acquired (cancer, AIDS and the like).

During the past 30 years, numerous tools have been developed which allow the introduction of various heterologous genes into cells, in particular mammalian cells. These different techniques may be divided into two categories. The first category relates to physical techniques such as microinjection, electroporation or particle bombardment which, although effective, are greatly limited to applications in vitro and whose implementation is cumbersome and delicate. The second category involves techniques relating to molecular and cell biology in which the gene to be transferred is combined with a vector of a biological or synthetic nature which promotes the introduction of said material.

Currently, the most effective vectors are viral, in particular adenoviral or retroviral, vectors. The techniques developed are based on the natural properties which these viruses have to cross the cell membranes, to escape degradation of their genetic material and to cause their genome to penetrate into the nucleus. These viruses have already been the subject of numerous studies and some of them are already used experimentally as vectors for genes in humans for the purpose, for example, of a vaccination, an immunotherapy or a therapy intended to make up for a genetic deficiency. However, this viral approach has many limitations, in particular because of the limited capacity for cloning into the viral genome, the risks of spreading in the host organism and in the environment the infectious viral particles produced, the risk of artefactual mutagenesis by insertion into the host cell in the case of retroviral vectors, and the high induction of immune and inflammatory responses in vivo during the therapeutic treatment, considerably limiting the number of administrations which can be envisaged (McCoy et al., 1995, Human Gene Therapy, 6, 1553–1560; Yang et al., 1996, Immunity, 1, 433–442). These numerous disadvantages, in particular in the context of a use in humans, have led several teams to develop alternative systems of transferring polynucleotides.

Several non-viral methods are currently available. By way of example, there may be mentioned coprecipitation with calcium phosphate, the use of receptors mimicking viral systems (for a review see Cotten and Wagner, 1993, Current Opinion in Biotechnology, 4, 705–710), or the use of polymers such as polyamidoamine (Haensler and Szoka, 1993, Bioconjugate Chem., 4, 372–379) or of polymer such as those presented in WO 95/24221 describing the use of dendritic polymers, the document WO 96/02655 describing the use of polyethyleneimine, or of polypropyleneimine and the documents U.S. Pat. No. 5,595,897 and FR 2,719,316 describing the use of conjugates of polylysine. Other non-viral techniques are based on the use of liposomes whose value as agent allowing the introduction, into cells, of certain biological macromolecules, such as for example DNA, RNA, proteins or certain pharmaceutically active substances, has been widely described in the literature. To this end, several teams have already proposed the use of cationic lipids which have a high affinity for the cell membranes and/or the nucleic acids. Indeed, although it has been shown, in the case of nucleic acids, that this type of macromolecule is capable of crossing the plasma membrane of some cells in vivo (WO 90/11092), it is nevertheless the case that the observed transfection efficiency is still highly limited, because of in particular the polyanionic nature of the nucleic acids which prevent their passage across the cell membrane, which itself has a negative net apparent charge. Since 1989 (Felgner et al., Nature, 337, 387–388), cationic lipids have been presented as molecules which are advantageous for promoting the introduction of large anionic molecules, such as nucleic acids, into certain cells. These cationic lipids are capable of complexing anionic molecules, thus tending to neutralize the negative charges on said molecules and to promote their coming close to the cells. Many teams have already developed various cationic lipids. By way of example, there may be mentioned DOTMA (Felgner et al., 1987, PNAS, 84, 7413–7417), DOGS or Transfectam™ (Behr et al., 1989, PNAS, 86, 6982–6986), DMRIE and DORIE (Felgner et al., 1993, Methods 5, 67–75), DC-CHOL (Gao et Huang, 1991, BBRC, 179, 280–285), DOTAP™ (McLachlan et al., 1995, Gene Therapy, 2,674–622) or Lipofectamine™, as well as those described in Patent Applications WO9116024 or WO9514651.

More particularly, Application WO9405624 describes cationic lipids of formula:

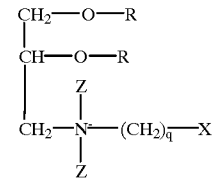

in which the R radicals are in particular octadecenyl radicals, the Z radicals are $C_1$–$C_{13}$ alkyl or —C(=O)-($C_1$–$C_{13}$) alkyl or acyl radicals, q is an integer from 1 to 6, X is in particular a short polyamine chain, such as spermine, spermidine, carboxyspermine or polylysine.

Applications EP 685457 and EP 685234 describe in particular cationic compounds of formula:

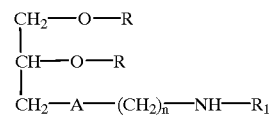

in which R is in particular a hydrocarbon chain having 10 to 30 carbon atoms, saturated or otherwise, A may in particular be chosen from the groups —O—(C=O)— and —NH—(C=O)—, n varies from 0 to 4 and $R_1$ is an alkyl or a short aminoalkyl chain in which the primary amine is substituted with an alkyl having 2 to 8 carbon atoms. These compounds have a low hemolytic activity and make it possible in vitro to introduce into HelaS3 cells a double-stranded RNA capable of acting as growth inhibiting agent.

Application DE 19521412 describes compounds which also comprise a nonpolar part and a polar part of formula:

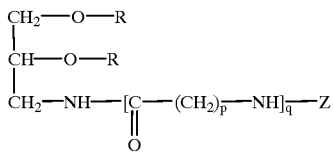

in which p varies from 1 to 6, q varies from 0 to 2, R is either C(=O)-C1–23 or C1–23, saturated or otherwise, and Z is a peptide, an aminoacid or a branched amino structure. These cationic compounds allow the in vitro transfection of cells in culture.

However, several studies (by way of example, see Mahato et al., J. Pharm. Sci., 1995, 84, 1267–1271, Thierry et al., 1995, P.N.A.S., 92, 9742–9746) have demonstrated that the efficiency of transferring the anionic macromolecule into cells could vary depending in particular on the interaction between the complexes and the cell membranes, the cell considered, the lipid composition of the cationic compounds, the size of the complexes formed with the anionic molecules and more particularly the ratio between the positive and negative charges on the different components of said complex. The mechanisms which allow in particular the interaction of the complexes with the cell membranes and the transfer of the complexes into the cell are still to a large extent poorly understood and researchers proceed in their studies based on a highly empirical approach. It is consequently desirable to provide other cationic lipids possibly having improved properties or properties which are different from the cationic lipids already described.

The Applicant has now identified new glycerolipid compounds, which can be provided in cationic form, useful in particular for transferring an active substance comprising negative charges, in particular a polynucleotide, into a target cell, whose use may be envisaged in particular in vivo in the context of a gene therapy.

Accordingly, the subject of the present invention is first of all a compound of formula:

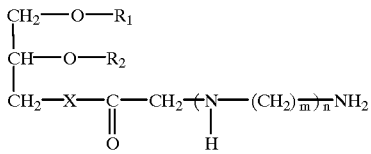

I in which:

$R_1$ and $R_2$, which are identical or different, are alkyl or alkenyl radicals having 6 to 23 carbon atoms (noted $C_6$–$C_{23}$), which are linear or branched, or radicals —C(=O)-($C_6$–$C_{23}$) alkyl or —C(=O)-($C_6$–$C_{23}$) alkenyl, or more particularly —C(=O)-($C_{12}$–$C_{20}$) alkyl or —C(=O)-($C_{12}$–$C_{20}$) alkenyl, which are linear or branched, aryl radicals, cycloalkyl radicals, fluoroalkyl radicals, oxyethylene or oxymethylene groups which are optionally repeated, linear or branched, optionally substituted, X is an oxygen atom or an amino radical —NR$_3$, R$_3$ being a hydrogen atom or an alkyl radical having 1 to 4 carbon atoms, n is a positive integer from 1 to 6, preferably from 2 to 4, m is a positive integer from 1 to 6, preferably from 2 to 4, and when n>1, m may be identical or different from said n.

The term "alkenyl" is intended to indicate that the carbon chain in question may comprise one or more double bond(s) along said chain.

According to a specific case of the invention, said compounds are characterized in that R1 and/or R2 are fluorinated, that is to say that at least one carbon of the polycarbon chain is substituted by a fluorinated group. Examples of such molecules are provided in Example N. In this specific case, the number of fluorinated carbon atoms on each chain $R_1$ or $R_2$ may vary from 1 to 12, and more particularly from 4 to 8, and is preferably 4. According to an advantageous case, R1 and/or R2 are alkyl radicals having 15 carbon atoms and the number of fluorinated carbon atoms is 4 for each of the relevant chains $R_1$ and $R_2$. The number of fluorinated groups present on the chains $R_1$ and/or $R_2$ may in particular vary from 1 to 23, more particularly from 9 to 17 and preferably is 9.

The compounds according to the invention may, in addition, be substituted. Such substitutions may in particular consist of a labeling molecule (see labeling molecules in U.S. Pat. No. 4,711,955) which makes it possible, for example, to visualize the distribution of the compounds or of the complexes containing them after administration in vitro or in vivo, a cell targeting molecule or an anchoring molecule. The inventor consequently also relates to a compound as presented above, conjugated with one or more targeting components via the intermediacy of at least a) one of the carbon atoms, in particular chosen from those present on the groups $R_1$, $R_2$ and/or $R_3$ or b) one of the secondary or primary nitrogen atoms of the polyamine chain. Such components may allow targeting to a specific cell type, facilitate penetration into the cell, lysis of the endosomes or alternatively intracellular transport and are widely described in the literature. They may be, for example, all or part of sugars, peptides (GRP peptide, Gastrin Releasing Peptide, for example), oligonucleotides, lipids, hormones, vitamins, antigens, antibodies, ligands specific for membrane receptors, ligands capable of reacting with an anti-ligand, fusogenic peptides, nuclear localization peptides, or a combination of such compounds. There may be mentioned more particularly the galactosyl residues which make it possible to target the asyaloglycoprotein receptor at the surface of hepatic cells, the fusogenic peptide INF-7 derived from the influenza virus hemagglutinin subunit HA-2 (Plank et al., 1994, J. Biol. Chem. 269, 12918–12924) or a nuclear localization signal derived from the SV40 virus T antigen (Lanford and Butel, 1984, Cell 37, 801–813) or the Epstein Barr virus EBNA-1 protein (Ambinder et al., 1991, J. Virol. 65, 1466–1478).

Such conjugates can be easily obtained by techniques widely described in the literature, and more particularly by chemical coupling, in particular using protecting groups such as trifluoroacetyl or Fmoc or Boc, onto the polyamine. The selective deprotection of a protecting group then makes it possible to couple the targeting component, and the glycerolipid is then deprotected. It should be stated, however, that the substitution of the nonreactive groups such as the carbon atoms in the CH or CH2 groups will be carried out during synthesis of the compounds of the invention by methods known to a person skilled in the art whereas the reactive groups, such as the primary or secondary amines, may be the subject of substitutions on the neosynthesized glycerolipids of the invention.

According to an advantageous case of the invention, said compound is in a cationic form, that is to say that it is in a form which is protonated by binding of a proton onto one or more nitrogen atoms present on the polyamine chain. In this case, said cationic glycerolipid is combined with one or more biologically acceptable anions, such as for example the trifluoroacetate, halide, monomethylsulfate, acetate or phosphate, iodide, chloride, or bromide anion and the like. It is also possible to obtain compounds in cationic form by substitution of the amines, for example, with a methyl or ethyl radical, and the like.

The compounds according to the present invention comprise from 2 to 7 positive charges, more particularly from 3 to 5, and preferably 5. It has been shown that the affinity of a polyamine for DNA depends in particular on the number of amine functional groups present on said polyamine (Braulin, W. H., Strick, T. J., and Record, M. T., Jr. (1982) Biopolymers 21, 1301–1314). Moreover, following their penetration into the cell by endocytosis, the complexes formed between a DNA and a cationic lipid compound are located in the endosomes in which the DNA may be degraded under the action of pH-dependent nucleases. To counter this phenomenon which affects the transfection efficiency, it is possible to use lysosomotropic agents, such as for example chloroquine, whose buffering capacity at pH 5.5 makes it possible to observe an improvement in the transfection. However, the efficiency of such compounds is not systematic; there may be noted, by way of negative examples, the cases of polyethyleimine (PEI), lipospermines or dendrimers of polyamidoamine (PAMAM). Moreover, the use of chloroquine at a high dose may present a toxic risk. According to the invention, the compounds possess a polyamine head which makes it possible to obtain a similar effect to that of the lysosomotropic molecules. A specific advantage of said compounds might consequently be to avoid the use of chloroquine for the in vivo applications.

According to a preferred embodiment of the invention, said compound is chosen from the group consisting of the following formulae:

II

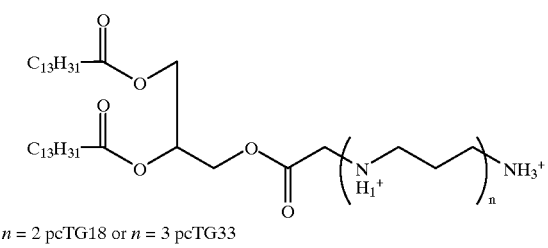

$n = 2$ pcTG18 or $n = 3$ pcTG33

III

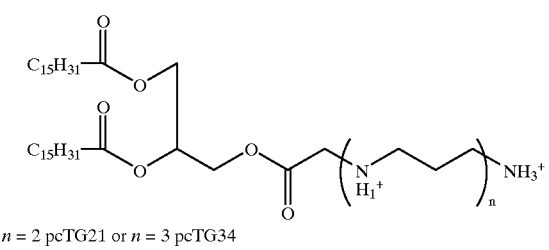

$n = 2$ pcTG21 or $n = 3$ pcTG34

IV

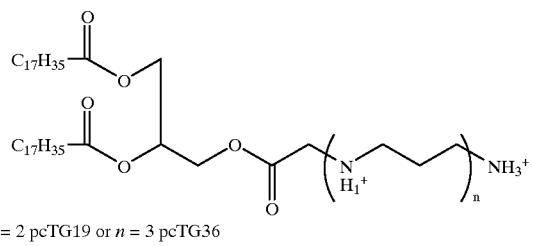

$n = 2$ pcTG19 or $n = 3$ pcTG36

V

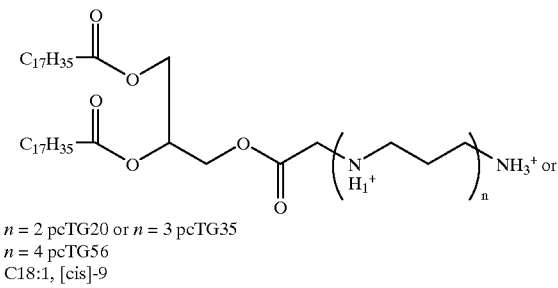

$n = 2$ pcTG20 or $n = 3$ pcTG35
$n = 4$ pcTG56
C18:1, [cis]-9

VI

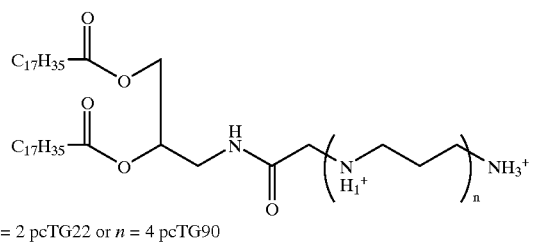

$n = 2$ pcTG22 or $n = 4$ pcTG90

These cationic compounds may, for example, be prepared by reacting a compound of formula:
These cationic compounds may, for example, be prepared by reacting a compound of formula:

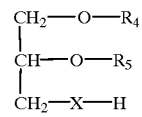

in which:
$R_4$ and $R_5$ are protecting groups forming in particular together an isopropylidene radical,
X has the same meaning as in formula I, with an acid of formula:

VII

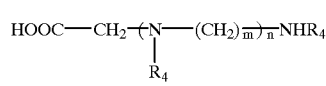

m and n having the same meaning as in formula I, $R_6$ being a protecting group, in particular t-butoxycarbonyl (BOC).

The functional groups O—$R_4$ and —O—$R_5$ are then deprotected so as to attach by esterification or etherification the radicals $R_1$ and $R_2$ in a known manner.

The compound obtained is deprotected in the presence of trifluoroacetic acid. The acid of formula VII is prepared in a known manner.

In the case of the compounds of the invention for which m=3, n=2 or 3, reference will be made to the examples indicated below in order to know the practical modalities for the synthesis. The processes described are applicable in general to the syntheses of the compounds according to the invention subject to adaptations within the capability of persons skilled in the art. However, the compounds of the invention cannot be limited to those obtained by the modes of preparation described above.

According to another aspect, the invention also relates to a composition comprising at least one compound as described above and optionally at least one adjuvant capable of enhancing the formation of the complex between a said compound and an active substance, or of enhancing the function of these complexes toward the cell.

Preferably, such an adjuvant will be a neutral or zwitterionic lipid which, for example, is or is derived from a triglyceride, a diglyceride, cholesterol (see for example U.S. Pat. No. 5,438,044), in particular, a neutral or zwitterionic lipid which is or is derived from a phosphatidylethanolamine (PE), phosphatidyl-choline, phosphocholine, sphyngomyelin, ceramide or cerebroside. Advantageously, dioleoylphosphatidylethanolamine (DOPE) will be chosen.

The weight ratio between the compound of the invention and the neutral or zwitterionic lipid is generally between 0.1 and 10, it being understood that this ratio may vary depending on the nature of the components considered. Persons skilled in the art have sufficient knowledge to allow these minor adaptations. It is also possible to use a mixture of neutral and/or zwitterionic lipids.

The invention relates, in addition, to a complex comprising at least one compound or at least one composition as described above and at least one active substance, in particular a therapeutically active substance, comprising at least one negative charge. According to a variant of the invention, said complex may, in addition, contain one or more cationic amphiphilic agents such as those described in the literature of which examples were provided above. In general, there will be used therapeutically active substances which may be used in particular in the context of gene therapy.

According to a specific embodiment, said active substance is chosen from nucleic acids and proteins. Preferably, the active substance of the complex according to the invention is a polynucleotide, said compound or said composition then making it possible to enhance the transfecting power of the polynucleotide in a cell.

"Polynucleotide" is understood to designate a DNA and/or RNA fragment which is double-stranded or single-stranded, linear or circular, natural, isolated or synthetic, designating a precise succession of nucleotides, which are modified or otherwise (see by way of example U.S. Pat. No. 5,525,711), labeled or otherwise (see for example U.S. Pat. No. 4,711,955 or EP 302175), making it possible to define a fragment or a region of a nucleic acid without size limitation. Polynucleotide is understood to designate in particular a cDNA, a genomic DNA, a plasmid DNA, a messenger RNA, an antisense RNA, a ribozyme, a transfer RNA, a ribosomal RNA or a DNA encoding such RNAs. "Polynucleotide" or "nucleic acid" are synonymous terms in the context of the present application.

According to a specific embodiment of the invention, said polynucleotide comprises a gene of interest and components allowing the expression of said gene of interest. In this embodiment, said polynucleotide is advantageously in the form of a plasmid. The components allowing expression are all the components allowing the transcription of said DNA fragment into RNA (antisense RNA or mRNA) and the translation of the mRNA into a polypeptide. They are in particular promoter sequences and/or regulatory sequences which are effective in said cell, and optionally the sequences required to allow excretion or expression of said polypeptide at the surface of the target cells. By way of example, there may be mentioned promoters such as the promoters of the viruses RSV, MPSV, SV40, CMV or 7.5 k, of the vaccinia virus, the promoters of the gene encoding muscle creatine kinase, actin, or pulmonary surfactant. It is, in addition, possible to choose a promoter sequence specific for a given cell type or which can be activated under defined conditions. The literature provides a large amount of information relating to such promoter sequences. Moreover, said polynucleotide may comprise at least two sequences, which are identical or different, exhibiting a transcriptional promoter activity and/or at least two coding DNA sequences, which are identical or different, situated, relative to each other, contiguously, far apart, in the same direction or in the opposite direction, as long as the transcriptional promoter function or the transcription of said sequences is not affected. Likewise, it is possible to introduce into this type of nucleic acid construct "neutral" nucleic sequences or introns which do not affect transcription and are spliced before the translation step. Such sequences and their uses are described in the literature. Said polynucleotide may also contain sequences required for intracellular transport, for replication and/or for integration. Such sequences are well known to persons skilled in the art. Moreover, the polynucleotides according to the present invention may also be polynucleotides which are modified such that it is not possible for them to become integrated into the genome of the target cell or polynucleotides which are stabilized with the aid of agents such as, for example, spermine.

In the context of the present invention, the polynucleotide may be homologous or heterologous to the target cell. It may be advantageous to use a polynucleotide which encodes all or part of a polypeptide, in particular a polypeptide having a therapeutic or prophylactic activity, and more particularly an immunogenic activity of the cellular or humoral type. The term polypeptide is understood without restriction as to its size or its degree of modification (for example glycosylation). There may be mentioned, by way of example, the genes encoding an enzyme, a hormone, a cytokine, a membrane receptor, a structural polypeptide, a polypeptide forming a membrane channel, a transport polypeptide, an adhesion molecule, a ligand, a factor for regulation of transcription, of translation, of replication, or of the stabilization of the transcripts, or an antibody, such as for example the gene encoding the CFTR protein, dystrophin, factor VIII or IX, E6/E7 of HPV, MUC1, BRAC1, β-interferon, γ-interferon, interleukin (IL)2, IL-4, IL-6, IL-7, IL-12, tumor necrosis factor (TNF) type alpha, GM-CSF (Granulocyte Macrophage Colony Stimulating Factor), the Herpes Simplex virus type 1 (HSV-1) tk gene, the gene associated with retino-blastoma or p53 or all or part of immunoglobulins, such as the fragments $F(ab)_2$, Fab', Fab or the anti-idiotypes (U.S. Pat. No. 4,699,880). This list is of course not limiting and other genes may be used.

According to a preferred embodiment, the complexes according to the invention are small in size (less than 500 nm, advantageously less than 200 nm and preferably less than 100 nm).

Moreover, the transfection experiments carried out show that advantageously the weight ratio of the lipid compound according to the invention to said polynucleotide is 0.01 to 100. The optimum ratio is between 0.05 and 10.

The invention also relates to a process for preparing the complexes cationic compounds/active substances comprising at least one negative charge, said process being characterized in that one or more compounds or compositions according to the invention are brought into contact with one or more active substances comprising at least one negative charge and in that said complex is recovered, optionally after a purification step.

In a first instance, according to a first variant, one or more cationic compounds are dissolved with an appropriate quantity of solvent or mixture of solvents which are miscible in water, in particular ethanol, dimethylsulfoxide (DMSO), or preferably a 1:1 (v:v) ethanol/DMSO mixture, so as to form lipid aggregates according to a known method described, for example, in Patent Application WO-A-9603977, or according to a second variant, are suspended with an appropriate quantity of a solution of detergent such as an octylglucoside such as n-octyl-β-D-glucopyranoside, or 6-O-(N-heptylcarbamoyl)-methyl-α-D-glucopyranoside.

The suspension may then be mixed with a solution of active substance comprising negative charges.

In the case where it is desirable that a neutral or zwitterionic lipid is present in the final complex, a film is formed, in the known manner, prior to the dissolution in the solvent which is miscible with water or in the solution of detergent, with a mixture containing a said cationic compound and a said neutral or zwitterionic lipid, such as for example DOPE.

One of the important characteristics of the process consists in the choice of the ratio between the positive charges of the cationic lipid and the negative charges of the active substance.

Without wishing to be limited by a specific ratio, quantities of the different charges will be chosen so that the ratio between the number of positive charges of the cationic compound or composition and the number of negative charges of the active substance is between 0.05 and 20, in particular between 0.1 and 15, and preferably between 5 and 10.

The calculation to arrive at such a ratio will take into consideration the negative charges carried by the active substance and the quantity of compound necessary to satisfy the ratio indicated above will be adjusted. The quantities and the concentrations for the other components are adjusted according to their respective molar masses and the number of their positive and/or negative charges.

This charge ratio also constitutes an advantageous characteristic of the complex according to the invention.

In the case of the second variant and optionally, subsequent dialysis may be carried out in order to reduce the detergent and to recover the complexes. The principle of such a method is for example described by Hofland et al. (1996, PNAS 93, p 7305–7309) and in chapter II of the Philippot et al. document (G. Gregoriadis, 81–89, CRC Press 1993).

It has been shown that the first variant leads to excellent results in terms of the size of the complexes obtained.

According to a third variant, one or more cationic compositions or compounds are suspended in a buffer and then the suspension is subjected to sonication until visual homogeneity is obtained. The lipid suspension is then extruded through two microporous membranes under appropriate pressure. The lipid suspension is then mixed with a solution of active substance comprising negative charges. This so-called sonication-extrusion technique is well known in the art.

The use of a neutral or zwitterionic lipid, such as DOPE, may prove advantageous for the production of complexes which are small in size (less than 200 nm, preferably less than 100 nm).

The characteristics of the complexes formed may be evaluated by several means which make it possible to determine, for example:

the state of complex formation with the active substance, in particular by identification of the free nucleic acids by agarose gel electrophoresis in the case where the substances are nucleic acids, the size of the particles by a quasi-elastic scattering of light, the absence of precipitation over the long term.

The object of the present invention is also the complexes obtained using the processes listed above.

The invention also relates to the use of a compound, of a composition or of a complex according to the invention to transfer at least one active substance, especially a therapeutically active substance, in particular a nucleic acid, into target cells, in vitro, ex vivo or in vivo, more particularly in vivo.

"Target cells" according to the invention is understood to mean prokaryotic cells, yeast cells and eukaryotic cells, plant cells, human or animal cells, and in particular mammalian cells. Cancer cells should, moreover, be mentioned. In vivo, the invention may be applied at the level of the interstitial or luminal space of tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilages and endothelium. According to an advantageous choice of the invention, the target cell will be a muscle cell, a hematopoietic stem cell or alternatively a cell of the airways, more particularly a tracheal or pulmonary cell, and advantageously a cell of a respiratory epithelium.

The invention also relates to a process for transferring in vitro a therapeutically active substance into a target cell according to which said cell is brought into contact with a complex according to the invention.

The complexes according to the invention can be used as a medicament for curative, preventive or vaccinal purposes. Accordingly, the subject of the invention is also the complexes of the invention as a medicament for curative, preventive or vaccinal purposes. Such complexes may be used in a method of therapeutic treatment which consists in transferring at least one therapeutically active substance, in particular a polynucleotide, into target cells, in particular a mammalian cell, and more precisely a muscle cell, a hematopoietic stem cell, a cell of the airways, more particularly a tracheal or pulmonary cell, a cell of the respiratory epithelium.

More widely, the present invention also relates to a process for introducing an active substance comprising negative charges into a cell, characterized in that cells cultured on an appropriate medium are brought into contact with a suspension of complexes cationic compound/active substance comprising negative charges. After a certain incubation time, the cells are washed and recovered. The introduction of the active substance may be checked (optionally after lysis of the cell) by any appropriate means.

The process of introduction is well known per se. The term "introduction" is understood to mean that the active substance comprising negative charges is transferred into the cell and is located, at the end of the process, inside said cell or at the level of the membrane thereof. In the case where the active substance is a nucleic acid, reference will be made more particularly to "transfection". In this case, the verification of the transfection of the nucleic acid can be carried out by any appropriate means, for example by measuring the expression of the gene considered or the concentration of the expressed protein.

The invention relates more particularly to the use of a compound, of a composition or of a complex according to the invention for the preparation of a medicament for curative, preventive or vaccinal purposes, intended for the treatment of the human or animal body, in particular by gene therapy.

According to a first possibility, the medicament may be administered directly in vivo (for example into a muscle, into the lungs by aerosol and the like). It is also possible to adopt the ex vivo approach which consists in collecting cells from the patient (bone marrow stem cells, peripheral blood lymphocytes, muscle cells and the like), transfecting them in vitro according to the present invention and readministering them to the patient.

The complexes according to the invention may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. There may also be mentioned the modes of administration by the topical route, such as for example by application of a cream, by oral administration or any other means perfectly known to the person skilled in the art and applicable to the present invention.

It is also within the scope of the invention to target specific organs or tissues by administration, in particular by the intravenous route, of a complex according to the invention prepared so as to adjust the ratio compound or composition/therapeutically active substance in said complex, the apparent charge of the complex (see in particular Liu et al., 1997, Gene Therapy, 4, 517–523; Thierry et al., 1995, P.N.A.S., 92, 9742–9746).

The invention also relates to a method of gene therapy consisting in administering to a patient an appropriate quantity of a composition according to the invention. According to the present invention and in the context of gene therapy in vivo, it is possible to repeat several times, in a given patient, the method as proposed without any major immune reaction being elicited against one of the compounds administered. The administration may take place in a single dose or repeated once or several times after a certain time interval. The repeated administration would make it possible to reduce the quantity of therapeutically active substance, more particularly of DNA, to be administered for a given dose. The appropriate route of administration and dosage vary according to various parameters, for example the individual or disease to be treated or alternatively the polynucleotide to be transferred.

The invention relates more particularly to a pharmaceutical preparation comprising at least one complex as described above, optionally containing, in addition, at least one adjuvant capable of stabilizing said pharmaceutical preparation for the purpose of its storage for example and/or of enhancing the transfecting power of said complex. Such an adjuvant could, for example, be chosen from the group consisting of chloroquine, a protic polar compound chosen in particular from propylene glycol, polyethylene glycol, glycerol, ethanol, 1-methyl-L-2-pyrrolidone or derivatives thereof, or an aprotic polar compound chosen in particular from dimethyl sulfoxide (DMSO), diethyl sulfoxide, di-n-propyl sulfoxide, dimethyl sulfone, sulfolane, dimethylformamide, dimethylacetamide, tetramethylurea, acetonitrile or derivatives thereof. Likewise, said preparation may contain a pharmaceutically acceptable carrier allowing its administration to humans or animals.

In the context of the use of a method of treatment in vivo according to the present invention, it is, in addition, possible to carry out, before the administration of a pharmaceutical preparation as described above, a treatment of the patient designed to observe a temporary depletion of the macrophages making it possible to enhance the transfection rate. Such a technique is described in the literature; see in particular Van Rooijen et al., 1997, TibTech, 15, 178–184.

The invention relates to a cell transfected with a complex as defined above, particularly a prokaryotic cell, a yeast cell or eukaryotic cell, especially an animal cell, in particular a mammalian cell, and more particularly a cancer cell. According to a preferred case of the invention, said cell is a cell of the airways, more particularly a tracheal or pulmonary cell, and advantageously a cell of the respiratory epithelium.

Finally, the invention relates to a device as well as a process allowing the isolation of a molecule of interest containing at least one negative charge, in particular nucleic acids as defined according to the present invention. "Isolation" is understood to designate the separation, detection, enrichment and purification of a fraction of anionic molecules, according to a specific or a specific method of isolation, qualitatively and/or quantitatively.

More particularly, the invention relates to a said device consisting of a disperse solid support, such as for example particles of polymers (of polystyrene, acrylamide, methacrylamide, or of one of their derivatives or any other polymer capable of forming particles of which numerous examples are described in the literature, in particular in the literature relating to diagnostic applications) or consisting of a nondispersed solid support such as, for example, a tube, for example made from polystyrene, a column, for example made from hydroxyapatite, a reversed phase column or an equivalent, onto which at least one compound or one composition according to the invention is bound in its cationic form. The binding to said solid support may be achieved in a direct (adsorption for example) or indirect (via a ligand/anti-ligand type coupling) manner. The production of such devices is within the capability of persons skilled in the art.

Moreover, the invention relates to a process using such a device so as to allow the isolation of anionic molecules, in particular of nucleic acids. Such an isolation may in particular be nonspecific or preferably specific. In this second case, said compound or said cationic composition is, prior to the isolation step, brought into contact with, for example, an oligonucleotide whose specific sequence makes it possible, after a hybridization step, under conditions allowing specific hybridization, to isolate in a specific manner a nucleic acid fragment containing all or part of a sequence complementary to the sequence of said oligonucleotide. The implementation of such a process is widely described in the literature.

LEGEND TO THE FIGURES

FIG. 1: This figure illustrates the mode of synthesis of the compounds described in A.

Figure 2B:
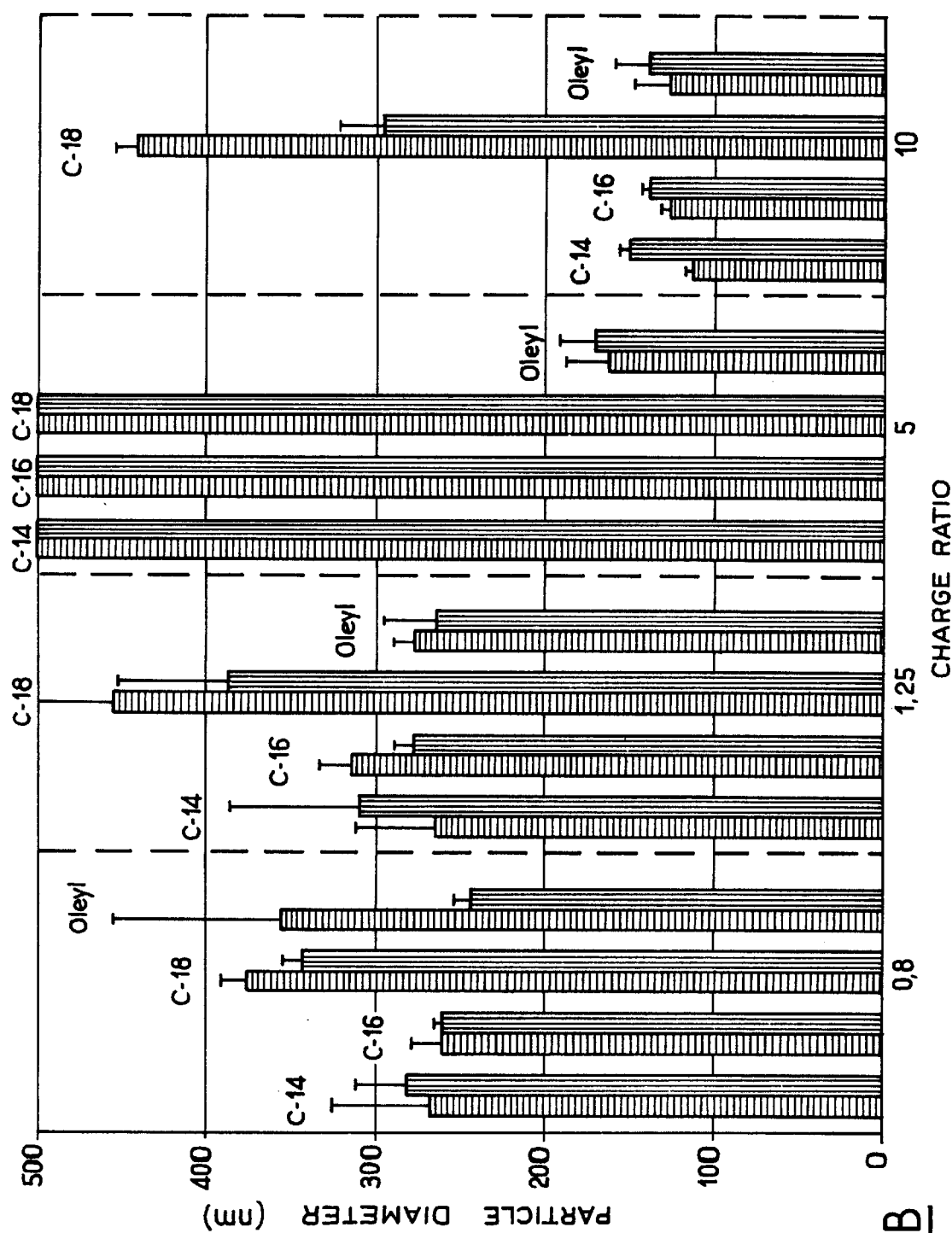
Figure 2C:
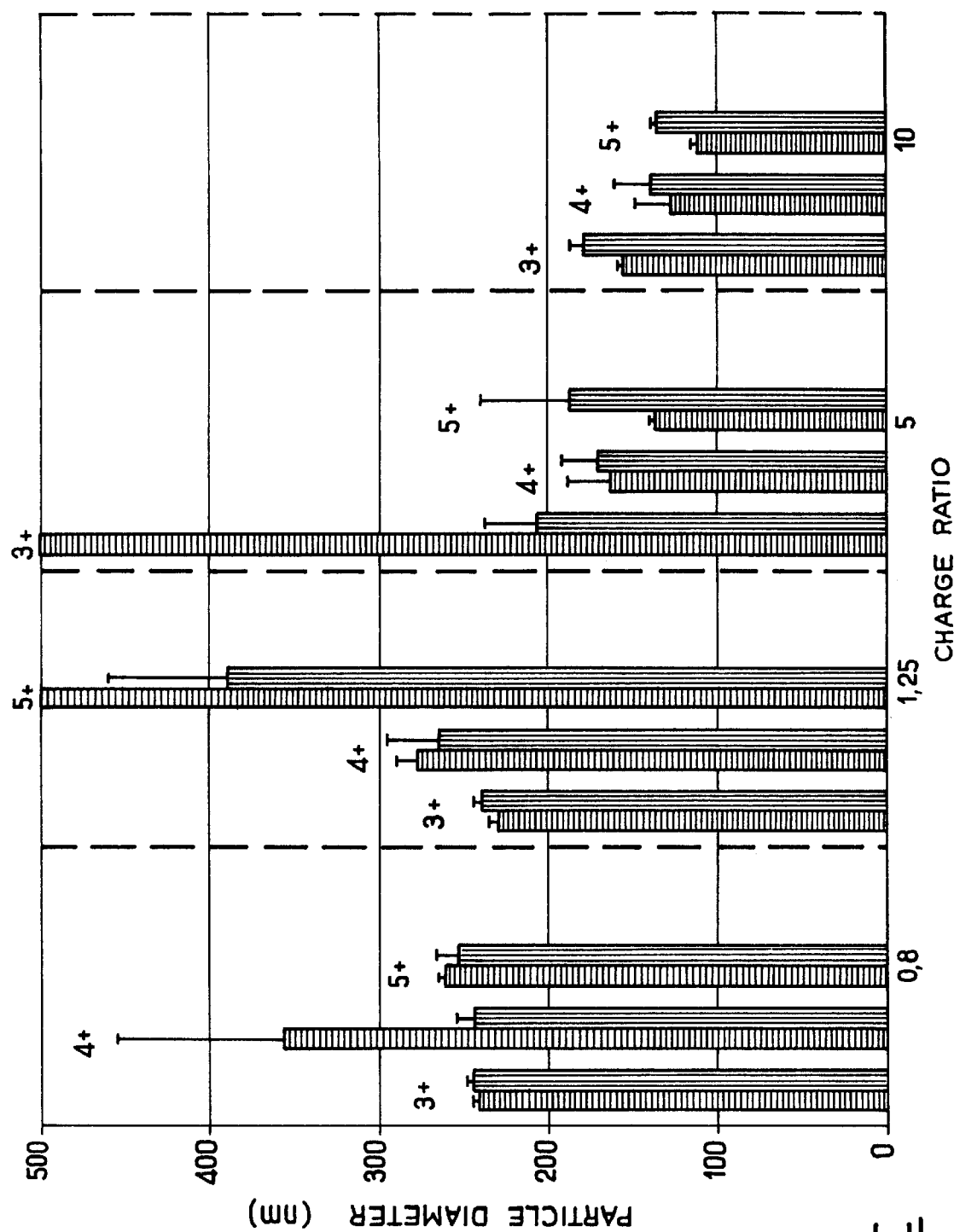

FIGS. 2A–C: Analysis of the size of the particles of complexes formed between the glycerolipids of the invention and the plasmid pTG11033 (Patent Application No. FR9708267) at 0.1 mg/ml which are prepared by the ethanol technique described above. The results are presented for different charge ratios. For each measurement, three independent preparations were tested and the measurement of reproducibility is evaluated by the standard deviation between these preparations. The size of the particles is measured by PCS (Photon Correlation Spectroscopy). The hatched columns show the complexes obtained in the absence of DOPE and the dark columns in the presence of an equimolar quantity of DOPE. The complexes for which precipitation is observed are represented by a column which extends over the scale. A) glycerolipids comprising 3 positive charges (C-14=pcTG 18, C-16=pcTG21, C-18=pcTG19, oleoyl=pcTG20); B) glycerolipids comprising 4 positive charges (C-14=pcTG 33, C-16=pcTG34, C-18=pcTG36, oleoyl=pcTG35); C) glycerolipids comprising oleoyl chains and 3 (pcTG20), 4 (pcTG35), or 5 positive charges (pcTG56).

FIG. 3: Intravenous injection of complexes according to the invention. The luciferase activity is indicated as RLU/mg of protein).

Figure 4:
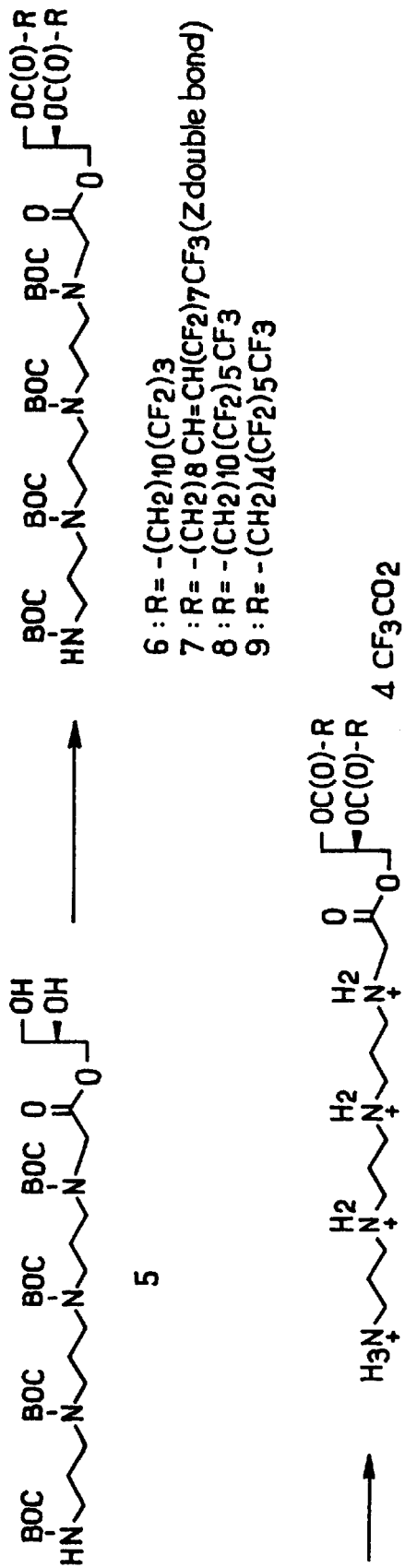

FIG. 4: This figure illustrates the mode of synthesis of the fluorinated glycerolipids of Example N.

FIGS. 5A to G: In vitro transfection of A549 cells in the presence of complexes containing different fluorinated glycerolipids according to the invention.

EXAMPLES

The examples below illustrate the invention, without limiting it in any manner, with reference to the accompanying figures which form an integral part of the description.
A. Synthesis of the Acids of Formula VII with m=3; n=2; $R_6$=BOC (acid 7a) or m=3; n=3; $R_6$=BOC (acid 7b) (see FIG. 1)

Amino acids 4, 6 and 15

A solution of acrylonitrile (9.6 ml, 146 mmol) in 50 ml of 1,4-dioxane is added dropwise to an ice-cold solution of glycine (10.0 g, 132 mmol) and 1 N sodium hydroxide (133 ml) in a 1/1 mixture of water and 1,4-dioxane (200 ml). The reaction medium is stirred at 0° C. for 1 h and at room temperature for an additional 4 h. A solution of di-tert-butyl dicarbonate (35.0 g, 159 mmol) in 1,4-dioxane (100 ml) is then added drop-wise and the reaction medium is stirred for two hours at room temperature. After extraction with ether (2×100 ml), the aqueous phase is acidified (pH 2–3) with 1 N hydrochloric acid and extracted with ethyl acetate (2×100 ml). The combined organic phases are dried and concentrated. The cyano acid obtained 1 (24.4 g, yield 81%) exists in the form of a white solid of melting point 87–89° C.

$^1$H-NMR (200 MHz, D$_2$O): δ 3.88 and 3.87 (2 s, 2 H, —CH$_2$—CO$_2$H), 3.48 and 3.45 (2 t, J=6.3 Hz, 2 H, —CH$_2$—N(BOC)—), 2.58 and 2.56 (2 t, J=6.3 and 6.4 Hz, 2 H, —CH$_2$—CN), 1.30 and 1.24 (2s, 9 H, t-Bu-).

A solution of acid 1 (11.5 g, 50.4 mmol) in 100 ml of ethanol containing 4.04 g (100 mmol) of sodium hydroxide is hydrogenated in the presence of Raney nickel (3.2 g) for 18 h at room temperature. The mixture is filtered on celite and the catalyst washed with methanol (2×30 ml). The filtrate is acidified to pH 4–5 with 10% hydrochloric acid and concentrated under vacuum to give a white solid which is dissolved in chloroform (50 ml) in order to precipitate most of the sodium chloride. After filtration, concentration of the filtrate under vacuum and recrystallization from carbon tetrachloride, amino acid 2 is obtained (10.4 g; yield 89%) whose melting point is 201–202° C.

$^1$H-NMR (200 MHz, D$_2$O): δ 3.53 (s, 2 H, —CH$_2$—CO$_2$H), 3.17 (t, J=6.6 Hz, 2 H, —CH$_2$—N(BOC)—), 2.83 (t, J=7.5 Hz, 2 H, —CH$_2$—NH$_2$), 1.69 (quint, J=7 Hz, 2 H, —CH$_2$—), 1.26 and 1.21 (2s, 9 H, t-Bu-).

The same procedure for the production of cyano acid 1 leads to the production of cyano acid 3 from amino acid 2.

$^1$H-NMR (200 MHz, CDCl$_3$): δ 4.00–3.85 (m, 2 H, —CH$_2$—CO$_2$H), 3.55–3.43 (m, 2 H, —CH$_2$—CH$_2$—CN), 3.31 (t, J=7.2 Hz, 4 H, —CH$_2$—N(BOC)—), 2.61 (m, 2 H, —CH$_2$—CN), 1.78 (quint, J=7.2 Hz, 2 H, —CH$_2$—), 1.47 and 1.44 (2s, 18 H, t-Bu-).

Amino acid 4 is obtained with a yield of 87% after purification by silica gel chromatography (eluent:methanol/dichloromethane 3/7, then 6/4) from cyano acid 3 according to the same procedure which led to amino acid 2. The melting point is 189–190° C.

$^1$H-NMR (200 MHz, D$_2$O): δ 3.57 and 3.54 (2s, 2 H, —CH$_2$—CO$_2$H), 3.2–3.0 (m, 6 H, —CH$_2$—N(BOC)—), 2.80 (t, J=7.7 Hz, 2 H, —CH$_2$—NH$_2$), 1.80–1.50 (m, 4 H, —CH$_2$—), 1.27 and 1.22 (2s, 18 H, t-Bu-).

The same procedure as for cyano acid 1 allows the production of cyano acid 5 from amino acid 4.

$^1$H-NMR (200 MHz, CDCl$_3$): δ 3.85 (broad s, 2H, —CH$_2$—CO$_2$H), 3.47 (t, J=6.6 Hz, 2 H, —CH$_2$—CH$_2$—CN), 3.35–3.05 (m, 8 H, —CH$_2$—N(BOC)—), 2.60 (m, 2 H, —CH$_2$—CN), 1.85–1.60 (m, 4 H, —CH$_2$—), 1.46 and 1.44 (2 s, 27 H, t-Bu-).

Amino acid 6 is obtained with a yield of 83% after purification by silica gel chromatography (eluent:methanol/dichloromethane 3/7, then 6/4) from cyano acid 5 according to the same procedure which led to amino acid 2.

$^1$H-NMR (200 MHz, D$_2$O): δ 3.76 and 3.73 (2s, 2 H, —CH$_2$—CO$_2$H), 3.25–2.75 (m, 12 H, —CH$_2$—N(BOC)— and —CH$_2$—NH$_2$), 1.85–1.50 (m, 6 H, —CH$_2$—), 1.28 and 1.23 (2s, 27 H, t-Bu-).

The same procedure as for cyano acid 1 allows the production of cyano acid 14 from amino acid 6.

$^1$H-NMR (200 MHz, CDCl$_3$): δ 3.95 and 3.87 (2 broad s, 2 H, —CH$_2$—CO$_2$H), 3.47 (t, J=6.5 Hz, 2 H, —CH$_2$—CH$_2$—CN), 3.40–3.05 (m, 12 H, —CH$_2$—N(BOC)—), 2.61 (m, 2 H, —CH$_2$—CN), 1.90–1.60 (m, 6 H, —CH$_2$—), 1.47, 1.45 and 1.44 (3 s, 36 H, t-Bu-).

Amino acid 15 is obtained with a yield of 71% after purification by silica gel chromatography (eluent:methanol/dichloromethane 1/9, then 3/7) from cyano acid 14 according to a procedure identical to that which led to amino acid 2.

$^1$H-NMR (200 MHz, D$_2$O-CD$_3$OD): δ 3.57 (m, 2 H, —CH$_2$—CO$_2$H), 3.15–2.80 (m, 14 H, —CH$_2$—N(BOC)—), 2.70 (t, J=7.5 Hz, 2 H, —CH$_2$—NH$_2$), 1.75–1.35 (m, 8 H, —CH$_2$—), 1.17 and 1.13 (2 s, 36 H, t-Bu-).

Acids 7a, 7b and 7c

A solution of di-tert-butyl dicarbonate (1.09 g, 5.01 mmol) in tetrahydrofuran (4 ml) is added to a solution of amino acid 4 (1.50 g, 3.85 mmol) and triethylamine (1.07 ml, 7.7 mmol) in a 1/1 mixture of tetrahydrofuran and water (8 ml). The reaction medium is stirred for 2 h at room temperature. It is then acidified to pH 3 with a 10% aqueous solution of hydrochloric acid and is extracted with ethyl acetate. The organic phase is washed with water, dried over sodium sulfate and concentrated to give a colorless oil which, after chromatography on a silica gel column (eluent:ethyl acetate), gives acid 7a (1.79 g; yield: 95%).

$^1$H-NMR (200 MHz, CD$_3$OD): δ 3.79 (s, 2 H, —CH$_2$—CO$_2$H), 3.30–3.15 (m, 6 H, —CH$_2$—N(BOC)—), 3.03 (t, J=6.7 Hz, 2 H, —CH$_2$—N(BOC)—), 1.85–1.60 (m, 4 H, —CH$_2$—), 1.46 and 1.43 (2 s, 27 H, t-Bu-).

The same procedure as for acid 7a allows the production of acid 7b (7.31 g; yield: 95%) from amino acid 6 (6.50 g).

$^1$H-NMR (200 MHz, CDCl$_3$): δ 3.93 and 3.86 (m, 2 H, —CH$_2$—CO$_2$H), 3.40–3.05 (m, 12 H, —CH$_2$—N(BOC)—), 1.85–1.60 (m, 6 H, —CH$_2$—), 1.44 (broad s, 36 H, t-Bu).

The same procedure as for acid 7a allows the production of acid 7c (3.37 g; yield: 92% after silica gel chromatography; eluent:methanol/dichloromethane 5/95, then 10/90) from amino acid 15 (3.20 g; 4.55 mmol).

$^1$H-NMR (200 MHz, CDCl$_3$): δ 3.85 (m, 2 H, —CH$_2$—CO$_2$H), 3.45–3.05 (m, 16 H, —CH$_2$—N(BOC)—), 1.85–1.60 (m, 8 H, —CH$_2$—), 1.45, 1.44 and 1.43 (3 s, 45 H, t-Bu-).

Synthesis of Cationic Glycerolipids Esters 8a, 8b and 8c

A solution of dicyclohexylcarbodiimide (0.60 g, 2.9 mmol) in dry dichloromethane (1 ml) is added to a solution of acid 7a (1.10 g, 2.25 mmol), (S)-(+)-2,2-dimethyl-1,3-dioxolane-4-methanol (0.39 g, 2.9 mmol) and 4-(dimethylamino)pyridine (27 mg, 0.23 mmol) in dry dichloromethane (3 ml). The reaction mixture is stirred for 18 h at room temperature. The dicyclohexylurea precipitate is removed by filtration and the filtrate is concentrated under vacuum and then chromatographed on a silica gel column (eluent:ether/hexane 6/4) to give ester 8a (0.72 g; 53%).

$^1$H-NMR (200 MHz, CDCl$_3$): δ 4.40–4.02 (m, 4 H, —CH$_2$—O—), 3.98 and 3.90 (2 broad s, 2 H, —CH$_2$—CO$_2$—), 3.73 (m, 1 H, CH—O—), 3.35–3.00 (m, 8 H), 1.85–1.55 (m, 4 H, —CH$_2$—), 1.45, 1.43 and 1.42 (3 s, 30 H), 1.36 (s, 3 H, Me-).

The same procedure as for ester 8a allows the production of ester 8b (3.08 g; yield: 49%) from acid 7b (5.32 g, 8.22 mmol).

$^1$H-NMR (200 MHz, CDCl$_3$): δ 4.40–4.02 (m, 4 H, —CH$_2$—O—), 3.99 and 3.91 (2 broad s, 2 H, —CH$_2$CO$_2$—), 3.73 (m, 1 H, CH—O—), 3.32–3.00 (m, 12 H, —CH$_2$—N(BOC)—), 1.85–1.55 (m, 6 H, —CH$_2$—), 1.45, 1.44, 1.43 and 1.41 (4 s, 39 H, t-Bu- and Me), 1.36 (2 s, 3 H, Me-).

The same procedure as for ester 8a allows the production of ester 8c (1.73 g; yield: 95%) from acid 7c (1.60 g, 1.99 mmol).

$^1$H-NMR (200 MHz, CDCl$_3$): δ 4.35–4.04 (m, 4 H, CH$_2$—O—), 3.99 and 3.92 (2 s, 2 H, —CH$_2$—CO$_2$—), 3.74 (m, 1 H, >CH—O—), 3.30–3.00 (m, 16 H, —CH$_2$—N(BOC)—), 1.85–1.55 (m, 8 H, —CH$_2$—), 1.46, 1.45, 1.44 and 1.42 (4 s, 48 H, t-Bu- and Me-), 1.36 (s, 3 H, Me-).

Dihydroxyesters 9a, 9b and 9c

A solution of ester 8a (663 mg, 1.10 mmol) and 1 N hydrochloric acid (0.44 ml) in methanol (19 ml) is stirred for 16 h at room temperature. Triethylamine (0.5 ml) is then added to neutrality. Evaporation under vacuum, followed by chromatography on a silica gel column (eluent:ether then ethyl acetate) gives dihydroxyester 9a (497 mg; yield: 80%) in the form of a colorless oil.

$^1$H-NMR (200 MHz, CDCl$_3$): δ 4.26 (m, 2 H, —CH$_2$—OC(=O)—), 4.00–3.50 (m, 5 H, CH—OH, —CH$_2$OH and —CH$_2$—CO$_2$—), 3.40–3.00 (m, 8 H, —CH$_2$—N(BOC)—), 1.85–1.55 (m, 4 H, —CH$_2$—), 1.45 and 1.43 (2 s, 27 H, t-Bu-).

The same procedure as for dihydroxyester 9a allows the production of dihydroxyester 9b (340 mg; yield: 71%) from ester 8b (500 mg, 0.66 mmol).

$^1$H-NMR (200 MHz, CDCl$_3$): δ 4.26 (m, 2 H, —CH$_2$—OC(=O)—), 4.00–3.40 (m, 5 H, CH—OH, —CH$_2$OH and —CH$_2$—CO$_2$—), 3.40–3.00 (m, 12 H, —CH$_2$—N(BOC)—), 1.85–1.55 (m, 6 H, —CH$_2$—), 1.46, 1.45 and 1.43 (3 s, 36 H, t-Bu-).

The same procedure as for dihydroxyester 9a allows the production of dihydroxyester 9c (1.23 g; yield: 83% after silica gel chromatography; eluent:methanol/dichloromethane 5/95) from ester 8c (1.55 g; 1.69 mmol).

$^1$H-NMR (200 MHz, CDCl$_3$): δ 4.25 (m, 2 H, —CH$_2$—OC(=O)—), 4.00–3.40 (m, 5 H, CH—OH, —CH$_2$OH and —CH$_2$—CO$_2$—), 3.40–3.00 (m, 16 H, —CH$_2$—N(BOC)—), 1.90–1.60 (m, 8 H, —CH$_2$—), 1.46, 1.45, 1.44 and 1.42 (4 s, 45 H, t-Bu-).

Triesters 10a, 11a, 12a and 13a

A solution of dicyclohexylcarbodiimide (142 mg, 0.69 mmol) in dry dichloromethane (1 ml) is added to a 35 solution of dihydroxyester 9a (130 mg, 0.23 mmol), oleic acid (195 mg, 0.69 mmol; Fluka puriss.) and 4-(dimethylamino)pyridine (3 mg, 0.02 mmol) in dry dichloromethane (2 ml). The reaction medium is stirred for 16 h at room temperature. The dicyclohexylurea precipitate is removed by filtration and the filtrate is concentrated under vacuum and chromatographed on a silica gel column (eluent:ether/hexane 3/7, then 4/6) to give triester 10a (142 mg; 57%) in the form of a colorless oil.

$^1$H-NMR (200 MHz, CDCl$_3$): δ 5.34 (m, 4 H, —CH=), 5.26 (m, 1 H, CH—OC(=O)—), 4.40–4.05 (m, 4 H, —CH$_2$—OC(=O)—), 3.95 and 3.88 (2 m, 2 H, —N(BOC)—CH$_2$—CO$_2$—), 3.35–3.00 (m, 8 H, —CH$_2$—N(BOC)—), 2.31 (t, J=7.5 Hz, 4 H, —CH$_2$—CO$_2$—), 2.01 (m, 8 H, —CH$_2$—CH=), 1.85–1.50 (m, 8 H, —CH$_2$—), 1.46, 1.44 and 1.42 (3 s, 27 H, t-Bu-), 1.30 and 1.27 (2 broad s, 44 H, —CH$_2$—), 0.88 (t, J=6.4 Hz, 6 H, Me-).

The same procedure as for triester 10a makes it possible to obtain triesters 11a (yield: 65%), 12a (yield: 64%) and 13a (yield: 58%) from dihydroxyester 9a and respectively from myristic acid, palmitic acid and stearic acid.

11a $^1$H-NMR (200 MHz, CDCl$_3$): δ 5.26 (m, 1 H, CH—OC(=O)—), 4.45–4.05 (m, 4 H, —CH$_2$—OC(=O)—), 3.95 and 3.88 (2 m, 2 H, —N(BOC)—CH$_2$—CO$_2$—), 3.35–3.00 (m, 8 H, —CH$_2$—N(BOC)—), 2.31 (t, J=7.5 Hz, 4 H, —CH$_2$—CO$_2$—), 1.85–1.50 (m, 8 H, —CH$_2$—), 1.46, 1.44 and 1.42 (3 s, 27 H, t-Bu-), 1.26 (s, 40 H, —CH$_2$—), 0.88 (t, J=6.4 Hz, 6 H, Me-).

12a $^1$H-NMR (200 MHz, CDCl$_3$): δ 5.26 (m, 1 H, CH—OC(=O)—), 4.40–4.05 (m, 4 H, —CH$_2$—OC(=O)—), 3.95 and 3.88 (2 m, 2 H, —N(BOC)—CH$_2$—CO$_2$—), 3.35–3.00 (m, 8 H, —CH$_2$—N(BOC)—), 2.31 (t, J=7.5 Hz, 4 H, —CH$_2$—CO$_2$—), 1.85–1.50 (m, 8 H, —CH$_2$—), 1.46, 1.44 and 1.42 (3 s, 27 H, t-Bu-), 1.25 (s, 48 H, —CH$_2$—), 0.88 (t, J=6.4 Hz, 6 H, Me-).

13a $^1$H-NMR (200 MHz, CDCl$_3$): δ 5.26 (m, 1 H, CH—OC(=O)—), 4.40–4.05 (m, 4 H, —CH$_2$—OC(=O)—), 3.95 and 3.88 (2 m, 2 H, —N(BOC)—CH$_2$—CO$_2$—), 3.35–3.00 (m, 8 H, —CH$_2$—N(BOC)—), 2.31 (t, J=7.5 Hz, 4 H, —CH$_2$—CO$_2$—), 1.85–1.50 (m, 8 H, —CH$_2$—), 1.46, 1.44 and 1.42 (3 s, 27 H, t-Bu-), 1.26 (s, 56 H, —CH$_2$—), 0.88 (t, J=6.4 Hz, 6 H, Me-).

Triesters 10b, 11b, 12b and 13b

The same procedure as for triester 10a allows the production of triester 10b (137 mg; yield: 61%) from dihydroxyester 9b (130 mg, 0.18 mmol) and oleic acid (153 mg, 0.54 mmol; Fluka puriss.).

$^1$H-NMR (200 MHz, CDCl$_3$): δ 5.34 (m, 4 H, —CH=), 5.26 (m, 1 H, CH—OC(=O)—), 4.40–4.05 (m, 4 H, —CH$_2$—OC(=O)—), 3.96 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$), 2.01 (m, 8 H, —CH$_2$—CH=), 1.85–1.50 (m, 10 H, —CH$_2$—), 1.46, 1.45, 1.44 and 1.41 (4 s, 36 H, t-Bu-), 1.30 and 1.27 (2 broad s, 44 H, —CH$_2$—), 0.88 (t, J=6.4 Hz, 6 H, Me-).

The same procedure as for triester 10a makes it possible to obtain triesters 11b (yield: 64%), 12b (yield: 58%) and 13b (yield: 63%) from dihydroxyester 9b and respectively from myristic acid, palmitic acid and stearic acid.

11b $^1$H-NMR (200 MHz, CDCl$_3$): δ 5.26 (m, 1 H, CH—OC(=O)—), 4.40–4.05 (m, 4 H, —CH$_2$—OC(=O)—), 3.97 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$—), 1.85–1.50 (m, 10 H, —CH$_2$—), 1.46, 1.45, 1.44 and 1.41 (4 s, 27 H, t-Bu-), 1.26 (s, 40 H, —CH$_2$—), 0.88 (t, J=25 6.4 Hz, 6 H, Me-).

12b $^1$H-NMR (200 MHz, CDCl$_3$): δ5.26 (m, 1 H, CH—OC(=O)—), 4.40–4.05 (m, 4 H, —CH$_2$—OC(=O)—), 3.97 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$—), 1.85–1.50 (m, 10 H, —CH$_2$—), 1.46, 1.45, 1.44 and 1.41 (4 s, 27 H, t-Bu-), 1.25 (s, 48 H, —CH$_2$—), 0.88 (t, J=6.4 Hz, 6 H, Me-).

13b $^1$H-NMR (200 MHz, CDCl$_3$): δ 5.26 (m, 1 H, CH—OC(=O)—), 4.40–4.05 (m, 4 H, —CH$_2$—OC(=O)—), 3.97 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$—), 1.85–1.50 (m, 10 H, —CH$_2$—), 1.46, 1.45, 1.44 and 1.41 (3 s, 27 H, t-Bu-), 1.25 (s, 56 H, —CH$_2$—), 0.88 (t, J=6.4 Hz, 6 H, Me-).

Triesters 10c

The same procedure as for triester 10a allows the production of triester 10c (0.75 g; yield: 47%) from dihydroxyester 9c (1.00 g; 1.14 mmol) and oleic acid (0.97 g; 3.42 mmol; Fluka puriss.).

$^1$H-NMR (200 MHz, CDCl$_3$): δ 5.34 (m, 4 H, —CH=), 5.26 (m, 1 H, CH—OC(=O)—), 4.40–4.05 (m, 4 H, —CH$_2$—OC(=O)—), 3.95 and 3.89 (2 m, 2 H, —N(BOC)—CH$_2$—CO$_2$—), 3.35–3.00 (m, 16 H, —CH$_2$—N(BOC)—), 2.31 (t, J=7.5 Hz, 4 H, —CH$_2$—CO$_2$—), 2.01 (m, 8 H, —CH$_2$—CH=), 1.85–1.50 (m, 12 H, —CH$_2$—), 1.46, 1.44, 1.43 and 1.41 (4 s, 45 H, t-Bu-), 1.30 and 1.27 (2 broad s, 44 H, —CH$_2$—), 0.88 (t, J=6.4 Hz, 6 H, Me-).

Glycerolipids pcTG20

Triester 10a (120 mg, 0.11 mmol) in solution in dry dichloromethane (1 ml) is treated for 3 h with a 1/1 mixture of trifluoroacetic acid and dry dichloromethane (20 ml) at 0° C. Hexane (50 ml) is then added and the mixture is evaporated under vacuum and gives a film which is suspended (vortex) in distilled ether (5 to 10 ml). Filtration gives a white powder which is washed with ether and dried under vacuum to give the glycerolipid pcTG20 (124 mg; 99%). Melting point: decomposes at 160° C.

$^1$H-NMR (200 MHz, CDCl$_3$-CF$_3$CO$_2$D): δ 5.34 (m, 5 H, —CH= and CH—OC(=O)—), 4.60–4.15 (m, 4 H, —CH$_2$—OC(=O)—), 3.99 (broad s, 2 H, —NH$_2^\oplus$—CH$_2$—CO$_2$—), 3.45–3.20 (m, 8 H, —CH$_2$—NH$_2^\oplus$—), 2.39 (t, J=7.5 Hz, 4 H, —CH$_2$—CO$_2$—), 2.50–2.20 (m, 4 H, —CH$_2$—CH$_2^\oplus$—NH$_2^\oplus$—), 2.01 (m, 8 H, —CH$_2$—CH=), 1.61 (m, 4 H, —CH$_2$—CH$_2$—CO$_2$—), 1.30 and 1.27 (2 s, 44 H, —CH$_2$—), 0.88 (t, J=6.4 Hz, 6 H, Me-).

Elemental analysis: calculated for C$_{53}$H$_{92}$F$_9$N$_3$O$_{12}$: C, 56.12%; H, 8.18%; N, 3.70%. Found: C, 56.3%; H, 7.9%; N, 3.7%.

Glycerolipid pcTG35

The same procedure as for the cationic lipid pcTG20 allows the production of the cationic lipid pcTG35 (101 mg; yield: 97%) from triester 10b (100 mg, 0.08 mmol). Melting point: decomposes at 190° C. $^1$H-NMR (200 MHz, CDCl$_3$-CF$_3$CO$_2$D): δ 5.35 (m, 5 H, —CH= and CH—OC(=O)—), 4.60–4.15 (m, 4 H, —CH$_2$—OC(=O)—), 4.00 (broad s, 2 H, —NH$_2^\oplus$—CH$_2$—CO$_2$—), 3.45–3.10 (m, 12 H, —CH$_2$—NH$_2^\oplus$—), 2.40 (t, J=7.5 Hz, 4 H, —CH$_2$—CO$_2$—), 2.45–2.20 (m, 6 H, —CH$_2$—CH$_2$—NH$_2^\oplus$—), 2.01 (m, 8 H, —CH$_2$—CH=), 1.60 (m, 4 H, —CH$_2$—CH$_2$—CO$_2$—), 1.30 and 1.27 (2 s, 44 H, —CH$_2$—), 0.87 (t, J=6.4 Hz, 6 H, Me-).

Elemental analysis: calculated for C$_{58}$H$_{100}$F$_{12}$N$_4$O$_{14}$: C, 53.36%; H, 7.72%; N, 4.29%. Found: C, 53.2%; H, 7.6%; N, 4.3%. The mass spectrum was measured at 849.8 Da (calculated: 849.3 Da).

Glycerolipid pcTG56

The same procedure as for the glycerolipid pcTG20 allows the production of the glycerolipid pcTG56 (0.51 g; yield: 93%) from triester 10c (0.52 g; 0.37 mmol). Melting point: decomposes at 220° C.

$^1$H-NMR (200 MHz, CDCl$_3$-CF$_3$CO$_2$D) δ 5.36 (m, 5 H, —CH= and CH—OC(=O)—), 4.60–4.15 (m, 4 H, —CH$_2$—OC(=O)—), 4.00 (broad s, 2 H, —NH$_2^\oplus$—CH$_2$—CO$_2$—), 3.45–3.10 (m, 16 H, —CH$_2$—NH$_2^\oplus$—), 2.41 (t, J=7.5 Hz, 4 H, —CH$_2$—CO$_2$—), 2.28 (m, 8 H, —CH$_2$—NH$_2^\oplus$—), 2.01 (m, 8 H, —CH$_2$—CH=), 1.61 (m, 4 H, —CH$_2$—CH$_2$—CO$_2$—), 1.30 and 1.27 (2 s, 44 H, —CH$_2$—), 0.87 (t, J=6.4 Hz, 6 H, Me-).

Glycerolipids pcTG18, pcTG21 and pcTG19

The same procedure as for the glycerolipid pcTG20 makes it possible to obtain the glycerolipids pcTG18 (yield: 97%; solid; decomposes at 165° C.), pcTG21 (yield: 96%; solid; decomposes at 170° C.) and pcTG19 (yield: 92%; solid; decomposes at 186° C.) from respectively triesters 11a, 12a and 13a.

pcTG18 $^1$H-NMR (200 MHz, CDCl$_3$-CF$_3$CO$_2$D ): δ 5.35 (m, 1 H, CH—OC(=O)—), 4.60–4.15 (m, 4 H, —CH$_2$—OC(=O)—), 3.97 (broad s, 2 H, —NH$_2^\oplus$—CH$_2$—CO$_2$—), 3.45–3.15 (m, 8 H, —CH$_2$—NH$_2^\oplus$—), 2.38 (t, J=7.5 Hz, 4 H, —CH$_2$—CO$_2$—), 2.45–2.20 (m, 4 H, —CH$_2$—CH$_2$—NH$_2^\oplus$—), 1.60 (m, 4 H, —CH$_2$—CH$_2$—CO$_2$—), 1.25 (s, 40 H, —CH$_2$—), 0.87 (t, J=6.4 Hz, 6 H, Me-).

Mass spectrum: calculated 684.1 Da; measured 684.5 Da.

pcTG21 $^1$H-NMR (200 MHz, CDCl$_3$-CD$_3$OD ): δ 5.20 (m, 1 H, CH—OC(=O)), 4.45–4.00 (m, 4 H, —CH$_2$—OC(=O)—), 3.78 (broad s, 2 H, —NH$_2^\oplus$—CH$_2$—CO$_2$—), 3.15–2.40 (m, 8 H, —CH$_2$—NH$_2^\oplus$—), 2.24 (t, J=7.5 Hz, 4 H, —CH$_2$—CO$_2$—), 2.18–1.92 (m, 4 H, —CH$_2$—CH$_2$—NH$_2^\oplus$—), 1.52 (m, 4 H, —CH$_2$—CH$_2$—CO$_2$—), 1.17 (s, 48 H, —CH$_2$—), 0.79 (t, J=6.4 Hz, 6 H, Me-).

Mass spectrum: calculated: 740.2 Da; measured 740.6 Da.

pcTG19 $^1$H-NMR (200 MHz, CDCl$_3$-CF$_3$CO$_2$D ): δ 5.38 (m, 1 H, CH—OC(=O)—), 4.60–4.15 (m, 4 H, —CH$_2$—OC(=O)—), 4.01 (broad s, 2 H, —NH$_2^\oplus$—CH$_2$—CO$_2$—), 3.45–3.20 (m, 8 H, —CH$_2$—NH$_2^\oplus$—), 2.41 (t, J=7.5 Hz, 4H, —CH$_2$—CO$_2$—), 2.50–2.25 (m, 4 H, —CH$_2$—CH$_2$—NH$_2^\oplus$—), 1.61 (m, 4 H, —CH$_2$—CH$_2$—CO$_2$—), 1.26 (s, 56 H, —CH$_2$—), 0.88 (t, J=6.4 Hz, 6 H, Me-). Mass spectrum: calculated 796.3 Da; measured 796.8 Da.

Glycerolipids pcTG33, pcTG34 and pcTG36

The same procedure as for the glycerolipid pcTG20 makes it possible to obtain the glycerolipids pcTG33 (yield: 97%; solid; decomposes at 205° C.), pcTG34 (yield: 94%; solid; decomposes at 215° C.) and pcTG36 (yield: 92%; solid; decomposes at 220° C.) from respectively triesters 11b, 12b and 13b.

pcTG33 $^1$H-NMR (200 MHz, CDCl$_3$-CF$_3$CO$_2$D): δ 5.37 (m, 1 H, CH—OC(=O)—), 4.60–4.15 (m, 4 H, —CH$_2$—OC(=O)—), 4.00 (broad s, 2 H, —NH$_2^\oplus$—CH$_2$—CO$_2$—), 3.45–3.15 (m, 12 H, —CH$_2$—NH$^\oplus_2$—), 2.39 (t, J=7.5 Hz, 4 H, —CH$_2$—CO$_2$—), 2.45–2.17 (m, 6 H, —CH$_2$—CH$_2$—NH$_2^\oplus$—), 1.60 (m, 4 H, —CH$_2$—CH$_2$—CO$_2$—), 1.25 (s, 40 H, —CH$_2$—), 0.87 (t, J=6.4 Hz, 6 H, Me-).

Mass spectrum: calculated 741.2 Da; measured 741.6 Da.

pcTG34 $^1$H-NMR (200 MHz, CDCl$_3$-CF$_3$CO$_2$D): δ 5.37 (m,

1 H, CH—OC(=O)—), 4.60–4.15 (m, 4 H, —CH$_2$—OC(=O)—), 3.98 (broad s, 2 H, —NH$_2^\oplus$—CH$_2$—CO$_2$—), 3.45–3.10 (m, 12 H, —CH$_2$—NH$_2^\oplus$—), 2.39 (t, J=7.5 Hz, 4 H, —CH$_2$—CO$_2$—), 2.45–2.15 (m, 6 H, —CH$_2$—CH$_2$—NH$_2^\oplus$—), 1.60 (m, 4 H, —CH$_2$—CO$_2$—), 1.25 (s, 48 H, —CH$_2$—), 0.87 (t, J=6.4 Hz, 6 H, Me-).

Mass spectrum: calculated 797.3 Da; measured 797.8 Da. pcTG36 $^1$H-NMR (200 MHz, CDCl$_3$-CF$_3$CO$_2$D): δ 5.35 (m, 1 H, CH—OC(=O)—), 4.60–4.15 (m, 4 H, —CH$_2$—OC(=O)—), 3.98 (broad s, 2 H, —NH$_2^\oplus$—CH$_2$—CO$_2$—), 3.45–3.10 (m, 12 H, —CH$_2$—NH$_2^\oplus$—), 2.37 (t, J=7.5 Hz, 4 H, —CH$_2$—CO$_2$—), 2.45–2.15 (m, 6 H, —CH$_2$—CH$_2$—NH$_2^\oplus$—), 1.59 (m, 4 H, —CH$_2$—CH$_2$—CO$_2$—), 1.25 (s, 56 H, —CH$_2$—), 0.87 (t, J=6.4 Hz, 6 H, Me-). Mass spectrum: calculated 854.4 Da; measured 854.0 Da.

Glycerolipid pcTG22

A slightly different route to that described above allowed the production of the glycerolipid pcTG22 from 3-amino-1,2-propanediol.

$^1$H-NMR (200 MHz, CDCl$_3$-CD$_3$OD): δ 5.04 (m, 1 H, CH—OC(=O)—), 4.27–3.92 (m, 2 H, —CH$_2$—OC(=O)—), 3.63 (broad s, 2 H, —CH$_2$—C(=O)—NH—), 3.10–2.90 (m, 8 H, —CH$_2$—NH$_2^\oplus$—), 2.24 and 2.23 (2 t, J=7.5 Hz, 4 H, —CH$_2$—CO$_2$—), 2.15–1.95 (m, 4 H, —CH$_2$—CH$_2$—NH$_2^\oplus$), 1.51 (m, 4 H, —CH$_2$—CH$_2$—CO$_2$—), 1.17 (s, 56 H, —CH$_2$—), 0.79 (t, J=6.7 Hz, 6 H, Me-). Mass spectrum: calculated 795.3 Da; measured 795.3 Da.

Glycerolipid pcTG90

A procedure similar to that described for the synthesis of the lipid pcTG56 allows the production of the lipid pcTG90 using 3-amino-1,2-propanediol in place of glycerol.

B: Preparation of the Glycerolipid-DNA Complexes by Dissolution in Ethanol

1. Preparation of the Complexes Glycerolipids pcTG20, Optionally DOPE,-DNA

The quantities of lipids are calculated based on the concentration of final DNA (0.1 mg/ml for the tests in cell cultures), the desired charge ratio, the molar mass and the number of positive charges of the chosen cationic lipid. To obtain a complex between pcTG20/DOPE and the plasmid DNA in a ratio of 10 between positive charges provided by the cationic lipid and negative charges provided by the DNA at a final DNA concentration of 0.1 mg/ml, the different ingredients are mixed according to the following calculation:

0.1 mg of DNA/ml, that is to say (0.1/330) mmol of negative charges (330 Da is the average molecular weight of a nucleotide) per ml correspond to: 0.30 μmol/ml of negative charges. To obtain 10 times more positive charges, a concentration of 3.0 μmol/ml of positive charges provided by the cationic lipid is required. The molar mass of pcTG20 in trifluoroacetate form is 1134 g/mol and the molecule content 3 positive charges. Therefore, 1.0 μmol/ml of pcTG20 is required, which corresponds to 1.13 mg/ml.

To obtain an equimolar concentration of L-α-dioleoyl-phosphatidylethanolamine (DOPE, 744 g/mol, Sigma; P0510), 0.74 mg/ml is required in the lipid preparation. The quantities and the concentrations for the other compounds are adjusted according to their respective molar masses and the number of their positive charges.

The lipids taken up in chloroform are evaporated and then solubilized in chloroform:methanol (v:v) and again evaporated. The cationic lipids are weighed and the quantity of DOPE is added from a stock solution of 10 or 20 mg/ml in chloroform to a glass tube sterilized with alcohol and with UV in order to obtain a cationic lipid concentration of 2 mM. The solvents are evaporated under vacuum (200 mbar) for 45 min at 45° C. using a vortex of 40 revolutions per minute (Labconco, Rapidvap, Uniequip, Martinsried, Germany). The lipid film is taken up in ethanol so as to be at the cationic lipid concentration of 50 mg/ml.

pcTG20/DOPE 1.13 mg +0.74 mg=1.87 mg in 23 μl of ethanol. This solution is adjusted to 230 μl with 20 mM HEPES pH 7.5 in order to prepare a cationic lipid solution at 5 mg/ml final.

The plasmid DNA is prepared in a plastic tube from a stock solution at 1 mg/ml (10 mM Tris, 1 mM EDTA, pH 7.5).

For a solution of 0.5 ml final, 50 μl of the stock solution (50 μg DNA) are collected to which 335 μl of 20 mM HEPES pH 7.5 are added. To complex the DNA with the lipid preparations, the lipids are added to the DNA. The suspension is mixed by aspiration/discharge using a pipette (10 times). The complexes are stored at +4° C.

115 μl of pcTG20/DOPE are added to the 385 μl of the DNA solution in order to obtain 0.5 ml of complex at 0.1 mg/ml DNA and at a charge ratio of 10.

The preparation of the complexes is carried out under a laminar flow cabinet.

The complexes are obtained whose characteristics are indicated in Table I below.

2. Preparation of the Complexes Glycerolipids pcT35, pcTG22 and pcTG18 Optionally DOPE,-DNA Based on the same protocol, the complexes are obtained whose characteristics are indicated in Table I below.

C. Preparation of the Glycerolipid-DNA Complexes by Suspension in a Detergent Solution 1. Preparation of the Complexes Glycerolipids pcTG20, Optionally DOPE,-DNA The quantities of lipids are calculated as described above based on the concentration of final DNA (0.1 mg/ml for the tests in vitro), the desired charge ratio, the molar mass and the number of positive charges of the cationic lipid chosen. The lipids are mixed in a glass tube, sterilized with alcohol and with UV, in order to obtain a 2 mM cationic lipid solution (see above). The solvents are evaporated and the lipid film is taken up in a solution of n-octyl, β-D-glucopyranoside (octylglucoside, Sigma, 0 9882) according to a cationic lipid/detergent ratio of 1:5 (mol:mol).

253 μl of a 20 mM octylglucoside solution in 20 mM HEPES pH 7.5 are collected and used to take up the film of pcTG20/DOPE lipid mixture. The plasmid DNA is prepared from a stock solution of plasmid DNA at 1 mg/ml of which 50 μl are placed in 0.5 ml (0.1 mg/ml final) to which 323.5 μl of 20 mM HEPES pH 7.5 are added. 126.5 μl of the lipid suspension are added to the DNA by aspirating and discharging 10 times using a pipette in order to obtain the final suspension at 0.1 mg/ml of DNA and a +/− charge ratio of 10. To remove the detergent, a dialysis of 3 times 4 hours at room temperature against 20 mM HEPES pH 7.5 is carried out in dialysis microbags (cut-off of 13.2 kD; Sartorius, Gottingen, Germany). The dialyzed DNA/lipid complexes are stored at +4° C. The preparation is carried out in a laminar flow cabinet.

The complexes are obtained whose characteristics are indicated in Table I below.

2. Preparation of the Complexes Glycerolipids pcTG35, Optionally DOPE,-DNA

The same protocol is applied as above.

D. Preparation of the Lipid-DNA Complexes by Sonication Extrusion

The quantities of lipids are calculated as described above based on the concentration of final DNA (0.1 mg/ml for the tests in vitro), the desired charge ratio, the molar mass and the number of positive charges of the cationic lipid chosen. The lipids are mixed in a glass tube, sterilized with alcohol and with UV, in order to obtain a 2 mM cationic lipid solution, as indicated above. The solvents are evaporated and the lipid film is taken up in 900 μl of 20 mM HEPES pH 7.5 at 4° C. for about 16 h. The suspension is sonicated in a sonication bath (Bransonic 221) to visual homogeneity.

The lipid suspension is extruded through two membranes with a pore diameter of 0.2 μm (Nucleopore, Costar, Cambridge, Mass., USA) and rinsed with 20 mM HEPES pH 7.5 (extruder from Lipex Biomembranes, Vancouver, Canada) at a maximum pressure of 50 bars. The lipid suspension is kept at room temperature for 1 hour. 450 μl of the lipid suspension are added to 50 μl of a stock solution of plasmid DNA (1 mg/ml) and mixed by aspirating/discharging 10 times using a pipette. The lipid/DNA complexes are stored at +4° C. The preparations are carried out under a laminar flow cabinet.

E. Protocol for Evaluation of the Complexing of the DNA by the Lipids

A 1% (w:v) agarose gel is prepared in a TAE buffer (TAE: Tris 4.8 g/l+sodium acetate 0.68 g/l+EDTA 0.336 g/l pH 7.8). If necessary, the sample is diluted in TAE and then the sample buffer (0.083% bromophenol blue, 0.083% cyanol xylene FF, 10% glycerol in water) is added so as to have 50 ngDNA/μl. The sample is briefly homogenized by vortex and left for 30 min at room temperature. As a control, the non-complexed plasmid prepared at the same concentration is used. 10 μl (500 ng of DNA) are deposited on the gel and the migration is carried out at 60 mV for 3 hours. The gel is developed in TAE containing 0.006% (v:v) of ethidium bromide at 10 mg/ml for at least 30 min. Next, the gel is rinsed in TAE and analyzed under UV.

F. Protocol for Measuring the Size of the Particles by Quasi-elastic Scattering of Light The analyses are carried out on a Coulter N4Plus (Coultronics France S. A., Margency, France) at 25° C. after equilibration of the sample for 20 min. An aliquot of the sample is aspirated and discharged several times before being pipetted. The sample is diluted in the measuring tank and homogenized. The measurement of the light diffracted at 90° is carried out for 180 sec after a 180 sec wait. The range used goes from 3 nm to 10,000 nm using 31 bins. To be valid, the sample should give between 50,000 and 1,000,000 counts/sec.

G. Physicochemical Characteristics

The three methods of formulation "injection of ethanol", "dialysis of detergent" and "sonication/extrusion" are applied to the cationic lipids according to the invention with or without equimolar quantities of DOPE at charge ratios of about 10, or 5. The formulations are considered to be appropriate when the DNA is completely complexed (no migration in the agarose gel) and when the complexes have a diameter, determined by quasi-elastic scattering of light, less than 500 nm. The table summarizes the results of these analyses. All the DNA/lipid complexes indicated in the table complex the DNA completely at the charge ratios analyzed.

TABLE I

| Cationic glycerolipid | Ratio[1] | Size (nm)[2] | Formulation |
| --- | --- | --- | --- |
| pcTG20/DOPE | 10 | 84 ± 20 | ethanol |
| pcTG20/DOPE | 10 | 212 ± 141 | detergent |
| pcTG20/DOPE | 5 | 96 ± 17 | ethanol |

TABLE I-continued

| Cationic glycerolipid | Ratio[1] | Size (nm)[2] | Formulation |
| --- | --- | --- | --- |
| pcTG35/DOPE | 10 | 67 ± 22 | ethanol |
| pcTG35/DOPE | 5 | 93 ± 39 | ethanol |
| pcTG35 | 10 | 83 ± 11 | ethanol |
| pcTG35 | 5 | 69[3] | ethanol |
| pcTG33 | 10 | 223 ± 138 | sonication |
| pcTG33/DOPE | 10 | 243 ± 172 | sonication |
| pcTG22 | 10 | 79 ± 59 | ethanol |
| pcTG22 | 5 | 87 ± 52 | ethanol |
| pcTG22/DOPE | 10 | 261 ± 98 | sonication |
| pcTG22/DOPE | 10 | 89 ± 146 | ethanol |
| pcTG22/DOPE | 5 | 72 ± 44 | ethanol |
| pcTG18 | 10 | 68 ± 53 | ethanol |
| pcTG18 | 5 | 72 ± 30 | ethanol |
| pcTG18/DOPE | 10 | 62 ± 43 | ethanol |
| pcTG18/DOPE | 5 | 109 ± 64 | ethanol |

[1]Ratio between the positive charges of the cationic lipid and the negative charges of the DNA.
[2]Determined 24 to 48 hours after the preparation (± represents the standard deviation of the measurement).
[3]Determined 8 days after the preparation These analyses show that the formulations meet the necessary requirements. The "injection of ethanol" method gives the best results for numerous preparations which are less than 100 nm in size. The methods by dialysis of detergent and sonication/detergent also make it possible to obtain complexes meeting the objectives of the present invention.

H. In Vitro Transfection of Satellite Cells

Cultures of dog muscle and human muscle cells are carried out in an HamF 14 medium (Life Technologies) supplemented with 10% fetal calf serum (FCS, Hyclone, Logan, Utah), 10 μg/ml of insulin (Sigma), 10 ng/ml of EGF (Sigma) and of FGF (Pepro Tech Inc, Rocky Hill, N.J.) 2 mM of glutamine (bioMérieux), and 40 μg/ml of gentamycin (Schering Plough).

The cells are inoculated 24 h to 48 h before the transfection into a 96-well culture plate with about $5 \times 10^3$ to $10^4$ cells per well, at about 30% confluence, and kept at 37° C. under a 5% $CO_2$ and 95% air atmosphere.

The transfections are carried out with mixtures of variable quantities of lipids and plasmid DNA in order to determine the charge ratios and the optimum DNA concentrations per well.

The complexes used are prepared 24 h to 48 h before the transfection and diluted in HamF 14 plus 40 μg/ml of gentamycin and 2 mM glutamine.

After removing the culture medium, 100 μl of transfection mixtures with or without 10% FCS are transferred into each of the wells and the plates are incubated for 4 h at 37° C.

All the transfection media are then adjusted to 10% FCS, 10 μg/ml of insulin (Sigma), 10 ng/ml of EGF (Sigma) and of FGF (Pepro Tech Inc, Rocky Hill, N.J.), 2 mM glutamine (bioMérieux), and 40 μg/ml of gentamycin (Schering Plough) for a final volume of 250 μl. The cultures are incubated for 48 h and then the cells are recovered and tested for their capacity to express the luciferase gene. The protein concentrations are determined by the system for testing quantity of protein (Promega).

I. Transfection of A549 Cells with Lipid Complexes

The A549 cells (epithelial cells derived from human pulmonary carcinoma) are cultured in Dulbecco's modified Eagle's medium (DMEM) containing 10% fetal calf serum (Gibco BRL) 24 hours before the start of the transfection in 96-well plates ($2 \times 10^4$ cells per well) in a humid atmosphere at 37° C. and 5% $CO_2$/95% air. For the transfection in the absence of serum, the medium is removed and replaced with serum-free medium. In another microplate, the following suspensions of lipid/DNA complexes are prepared (lipid/DNA complexes at 0.1 mg/ml of DNA and at the indicated charge ratio): 44 µl (4.4 µg DNA), 22 µl (2.2 µg DNA), 5.5 µl (0.55 µg DNA) of stock solution in the first 3 wells, and 11 µl (0.11 µg DNA) of the stock solution diluted 10-fold in the next well. The volume is adjusted to 110 µl with DMEM and 100 µl are transferred over the A549 cells. The incubation is carried out with 4, 2, 0.5 and 0.1 µg of DNA per well for 4 hours. Next, 50 µl of DMEM+30% fetal calf serum are added 4 hours after the start of transfection and then 100 µl of DMEM+10% FCS 24 hours after the start of transfection. The transfections in the presence of 10% fetal calf serum are carried out in an identical manner except that the transfection occurs in medium with serum.

J. Analysis of the Transfection 48 h after the transfection, the medium is removed and the cells are washed with 100 µl of PBS phosphate solution and lyzed with 50 µl of lysis buffer (Promega). The lysates are frozen at −80° C. until the expressed luciferase activity is measured. The latter is carried out on 20 µl of mixture for one minute using the "Luciferase" determination kit (Promega) (LB96P Berthold luminometer) in 96-well plates in kinetic mode.

K. Transfection in Vitro

A few of these preparations were evaluated in transfection in vitro using the A549 cells and the dog primary satellite cells.

The results are summarized in Table II below and show the relative light units (RLU) per well. The values given are obtained with 2 µg of DNA per well. All the complexes are prepared using the injection of ethanol method. The total protein concentration per well is determined by the conventional techniques (BCA test, Pierce). As a guide, a well contains about 20 to 30 µg of protein.

TABLE II

| Lipid | Ratio[1] | A549[2] | A549 + serum | myoblasts | myoblasts + serum |
| --- | --- | --- | --- | --- | --- |
| pcTG20/DOPE | 10 | $3.6 \times 10^5$ | $6.1 \times 10^6$ | $8.9 \times 10^6$ | $2.3 \times 10^7$ |
| pcTG20/DOPE | 5 | $8.25 \times 10^6$ | $2.8 \times 10^7$ | $8.8 \times 10^5$ | $1.3 \times 10^6$ |
| pcTG35/DOPE | 10 | $4 \times 10^6$ | $1.0 \times 10^7$ | $7.1 \times 10^3$ | $6.5 \times 10^7$ |
| pcTG35/DOPE | 5 | $3.3 \times 10^7$ | $6.8 \times 10^7$ | $4.3 \times 10^6$ | $1.0 \times 10^8$ |
| pcTG35 | 10 | $1.2 \times 10^8$ | $7.6 \times 10^6$ | $1.8 \times 10^7$ | $6.2 \times 10^8$ |
| pcTG35 | 5 | $1.6 \times 10^3$ | $6.6 \times 10^7$ | $3.4 \times 10^8$ | $1.7 \times 10^8$ |

[1]Ratio between the positive charges of the cationic lipid and the negative charges of the DNA.
[2]Free DNA between 0 and 270 relative light units.

The expression of luciferase (RLU/min) reported in mg of proteins gives the following values:

pcTG35 R+/−10 (A549) $3.4 \times 10^{10}$ RLU/min/mg protein pcTG35 R+/−5 (A549) $2.8 \times 10^{10}$ RLU/min/mg protein pcTG35/DOPEv R+/−5 (A549+serum) $1.0 \times 10^{10}$ RLU/min/mg protein The compounds pcTG20 and pcTG35 are capable of efficiently transfecting the two types of cells tested when they are complexed with the plasmid DNA. It will be noted that some formulations give higher results in the presence of serum and that the serum has no inhibitory effect on this type of preparation.

In the same manner, analyses of transfection in vitro which were carried out on A549 cells have made it possible to demonstrate a) that the compound pcTG90 complexed with a plasmid pTG11033 makes it possible to observe an efficient transfection under similar conditions to those described above in the absence or in the presence of DOPE, in the absence or in the presence of serum and b) to verify that DOPE could be substituted by another adjuvant such as for example 1,2-di-stearoyl-sn-glycerophosphoethanolamine (Avanti 850715), 1,2-di-phytanoyl-sn-glycero-3-phosphoethanolamine (Avanti 850402), 1,2-di-myristoyl-sn-glycero-3-phosphoethanolamine (Avanti 850745), 1,2-di-lauroyl-sn-glycero-3-phosphoethanolamine (Avanti 850702), 1,2-di-palmitoyl-sn-glycero-3-phosphoethanolamine (Avanti 850705), 1,2-di-elaidoyl-sn-glycero-3-phosphoethanolamine (Avanti 850725), 1,2-di-palmitoleyl-sn-glycero-3-phosphoethanolamine (Avanti 850706) or 1,2-di-linoleoyl-sn-glycero-3-phosphoethanolamine (Avanti 850755).

L. Analysis of the Size of the Particles (according to the protocol described in F).

The analyses carried out by PCS show that the size of the particles and their aggregation strongly depend on the charge ratio, the structure of the lipid as well as the presence or absence of DOPE.

Stable complexes of 100 to 200 nm were reproducibly obtained for a charge ratio of 10 when the cationic glycerolipid is in excess relative to the DNA (see FIGS. 2). The results show that only the complexes containing a C18 glycerolipid (pcTG19, pcTG36) have a problem of suspension, giving rise to large complexes whose size is variable. In contrast, the oleoyl-type lipids containing 4 or 5 charges (pcTG35, pcTG56) make it possible to obtain complexes of about 200 nm for a charge ratio of 5. Moreover, we showed that an equimolar quantity of DOPE slightly increases the size of the particles and reduces the tendency which the complexes have to aggregate at a low charge ratio (see FIGS. 2A and 2B). DOPE makes it possible, in addition, to obtain a stabilizing effect for the complexes containing C-14 or C-16 glycerolipids with three amine groups (FIG. 2A); this effect is not observed for the homologous compounds containing four amine functional groups (FIG. 2B). The tendency of the complexes to aggregate considerably increases for a charge ratio of 5, suggesting that the repulsions of charges is a decisive factor for avoiding the aggregation phenomenon. Comparison of the complexes containing glycerolipids carrying fatty acids of increasing length show minor differences between the C-14, C-16 and oleoyl derivatives for a charge ratio of 10, in particular in the case of the glycerolipids containing 4 amine groups. The number of amine groups at the level of the polar head of the glycerolipids containing oleoyls exhibits a slight effect on the size of the complexes (FIG. 2C).

It should be noted, in addition, that the results observed by this technique for measuring the size of the complexes were confirmed by electron microscopy.

M. Intravenous Injection of Complexes According to the Invention

The results are summarized in FIG. 3. Complexes according to the invention were synthesized according to the methods described above from the glycerolipids pcTG35, pcTG56 and pcTG90, in the presence of an equimolar quantity of DOPE, at a fixed charge ratio of 5, using a plasmid containing the gene for luciferase pTG11033 (French Patent Application No. 97/08267).

The mice used are 9 to 11-week old female C57BL/6 mice. The intravenous injections are performed in the tail after disinfecting the skin with 70% ethanol. The volume injected is 200 µl and the DNA concentration is 0.24 mg/ml (lipid concentration 10 mg/ml).

Two days after the injections, the mice are sacrificed. After extraction, the tissues are frozen in liquid nitrogen and stored at −80° C. In order to measure the luciferase activity, the tissues are mechanically ground with the aid of a pestle in a mortar placed on dry ice. 500 µl or 200 µl of lysis buffer (Promega) are added to the tissue debris obtained from lungs or trachea, respectively, and subjected to three freeze/thaw stages. The cellular debris is removed by centrifugation and the luciferase activity (in RLU/min, relative light unit per minute) is measured on 20 µl of supernatant in accordance with the manufacturer's instructions (Promega) by adding 100 µl of reagent and by measuring the activity by luminescence. The luciferase activity measured is standardized relative to the protein quantity with the aid of a calibration series prepared from commercially available luciferase (Promega). The total protein quantity is, moreover, determined by the colorimetric bicinchoninic acid BCA method (Smith et al., 1985, Anal. Biochem., 150, 76–85 Pierce) using one aliquot of supernatant. This makes it possible to express the luciferase activity in RLU per milligram of protein extracted from the tissues.

The results show that the expression of the luciferase reporter gene in the lungs after intravenous injection of complexes containing one of the three glycerolipids indicated above in the presence of DOPE is markedly enhanced relative to the injection of DNA alone by a factor of about 15 to 30 times. The values indicated are mean values obtained from 2 to 6 mice injected.

N Synthesis of Fluorinated Glycerolipids pcTG69 to pcTG72.

1. Synthesis of the Triesters (see FIG. 4)

Triester 6: 232 mg (1.12 mmol) of dicyclohexylcarbodiimide in 1 ml of dichloromethane are added to a solution of dihydroxyester 5 (270 mg, 0.37 mmol), fluorinated acid 1 (454 mg, 1.12 mmol) and 4-(dimethylamino)pyridine (5 mg, 0.038 mmol) in 4 ml of dichloromethane. The reaction is carried out with stirring for 16 hours at room temperature. The dicyclohexylurea precipitate is removed by filtration and the filtrate is concentrated under vacuum and subjected to chromatography on a silica gel column (eluent:ether:hexane, 4:6, v:v) so as to obtain triester 6 (275 mg, 48%) in the form of a viscous liquid. $^1$H-NMR (200 MHz, CDCl$_3$): δ 5.25 (m, 1 H, >CH—OC(O)—), 4.40–4.08 (m, 4 H, —CH$_2$—OC(O)—), 3.95 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$—), 2.20–1.88 (m, 4 H, —CH$_2$—CF$_2$—), 1.82–1.50 (m, 10 H, —CH$_2$—), 1.45, 1.44, 1.43 and 1.41 (4 s, 36 H, t-Bu-), 1.29 (br s, 28 H, —CH$_2$—), $^{19}$F NMR (376 MHz, CDCl$_3$): d −81.6, −115.1, −125.0, −126.5.

Triester 7: According to an identical protocol to that described for triester 6, triester 7 (220 mg, 49%) is obtained from dihydroxyester 5 (170 mg, 0.236 mmol) and fluorinated acid 2 (426 mg, 0.707 mmol).

$^1$H-NMR (200 MHz, CDCl$_3$): δ 6.40 (dtt, J=15.6, 6.9, 2.2 Hz, 2 H, =CH—CF$_2$—), 5.59 (dt, J=15.6, 12.3 Hz, 2 H, =CH—CH$_2$—), 5.25 (m, 1 H, >CH—OC(O)—), 4.40–4.05 (m, 4 H, —CH$_2$—OC(O)—), 3.96 and 3.89 (2 m, 2 H, —N(BOC)—CH$_2$—CO$_2$—), 3.35–3.00 (m, 12 H, —CH$_2$—N(BOC)—), 2.31 (t, J=7.2 Hz, 4 H, —CH$_2$—CO$_2$—), 2.20 (m, 4 H, allylic H), 1.80–1.50 (m, 10 H, —CH$_2$—), 1.45, 1.44, 1.43 and 1.41 (4 s, 36 H, t-Bu-), 1.30 (br s, 20 H, —CH$_2$—). $^{19}$F NMR (376 MHz, CDCl$_3$): d −81.3, −111.6, −121.9, −122.4, −123.2, −123.9, −126.6.

Triester 8: According to an identical protocol to that described for triester 6, triester 8 (230 mg, 47%) is obtained from dihydroxyester 5 (210 mg, 0.291 mmol) and fluorinated acid 3 (441 mg, 0.874 mmol).

$^1$H-NMR (200 MHz, CDCl$_3$) δ 5.25 (m, 1 H, >CH—OC(O)—), 4.40–4.10 (m, 4 H, —CH$_2$—OC(O)—), 3.95 and 3.89 (2 m, 2 H, —N(BOC)—CH$_2$—CO$_2$—), 3.35–3.00 (m, 12 H, —CH$_2$—N(BOC)—), 2.31 (t, J=7.5 Hz, 4 H, —CH$_2$—CO$_2$—), 2.20–1.90 (m, 4 H, —CH$_2$—CF$_2$—), 1.82–1.50 (m, 10 H, —CH$_2$—), 1.45, 1.44, 1.43 and 1.41 (4 s, 36 H, t-Bu-), 1.29 (br s, 28 H, —CH$_2$—). $^{19}$F NMR (376 MHz, CDCl$_3$): d −81.3, −114.9, −122.4, −123.2, −124.0, −126.6.

Triester 9: According to an identical protocol to that described for triester 6, triester 9 (165 mg, 49%) is obtained from dihydroxyester 5 (160 mg, 0.222 mmol) and fluorinated acid 4 (280 mg, 0.666 mmol).

$^1$H-NMR (200 MHz, CDCl$_3$): δ 5.25 (m, 1 H, >CH—OC(O)—), 4.45–4.08 (m, 4 H, —CH$_2$—OC(O)—), 3.95 and 3.89 (2 m, 2 H, —N(BOC)—CH$_2$—CO$_2$—), 3.35–3.00 (m, 12 H, —CH$_2$—N(BOC)—), 2.37 (m, 4 H, —CH$_2$—CO$_2$—), 2.26–1.95 (m, 4 H, —CH$_2$—CF$_2$—), 1.85–1.55 (m, 14 H, —CH$_2$—), 1.45, 1.44, 1.43 and 1.41 (4 s, 36 H, t-Bu-). $^{19}$F NMR (376 MHz, CDCl$_3$) d −81.3, −114.9, −122.4, −123.4, −124.1, −126.7.

2. Synthesis of pcTG69

Triester 6 (120 mg, 0.079 mmol) in 1 ml of dichloromethane is treated for 3 hours with 16 ml of a solution of trifluoroacetic acid and dichloromethane (1:1, v:v) at 0° C. 100 ml of hexane are added and the mixture is evaporated under vacuum so as to obtain a film which is taken up in distilled ether. After filtration, a white powder is obtained which is washed with ether and dried under vacuum to give the compound pcTG69 (115 mg, 94%). Mp=205° C.

3. Synthesis of pcTG70

The glycerolipid pcTG70 (185 mg, 86%) is obtained in the form of a white powder from triester 7 (210 mg, 0.111 mmol) according to a process identical to that described for pcTG69. Mp=210° C.

4. Synthesis of pcTG71

The glycerolipid pcTG71 (141 mg, 90%) is obtained in the form of a white powder from triester 8 (150 mg, 0.089 mmol) according to a process identical to that described for pcTG69. Mp=220° C.

5. Synthesis of pcTG72

The glycerolipid pcTG72 (87 mg, 92%) is obtained in the form of a white powder from triester 9 (90 mg, 0.06 mmol) according to a process identical to that described for pcTG69. Mp=220° C.

These fluorilated compounds correspond to the backbone of pcTG35 (4 amino groups) with a polycarbon chain of variable size (C11, C15, C17 or C19 unsaturated). They were synthesized according to the injection of ethanol method.

O. In Vitro Transfection of the Complexes Containing the Fluorilated Compounds

Figure 5A:
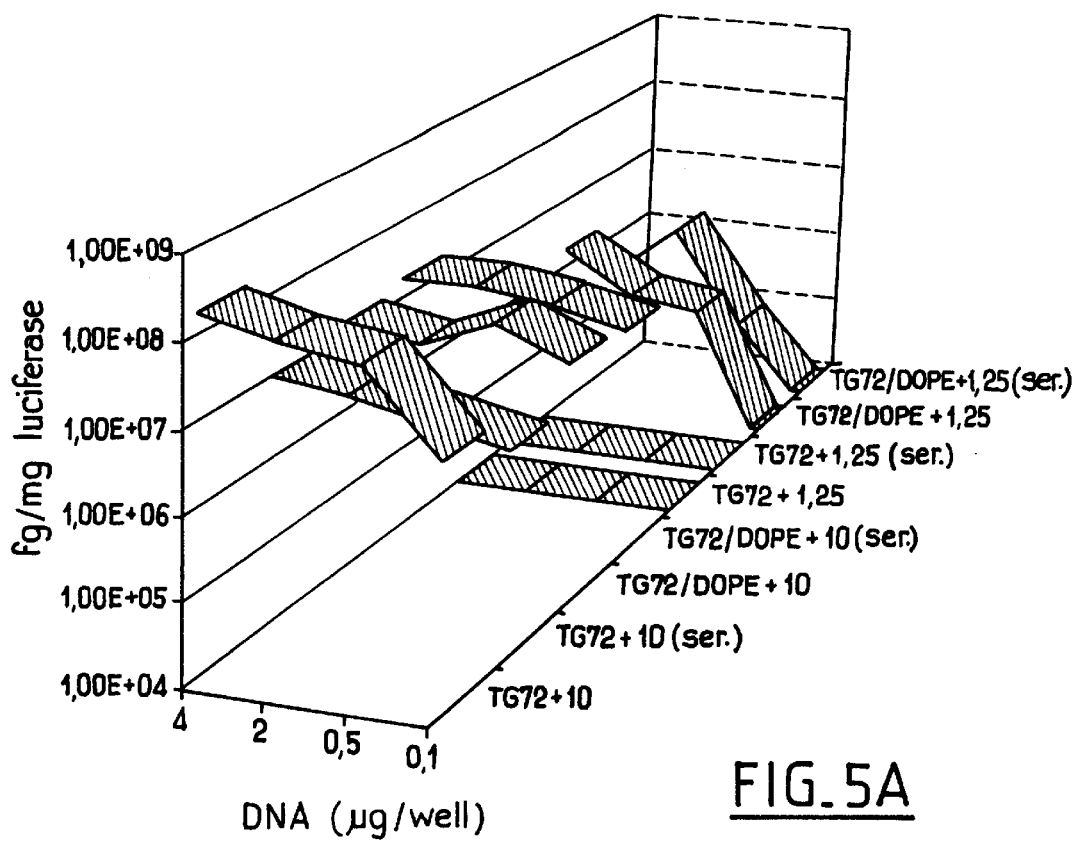
Figure 5B:
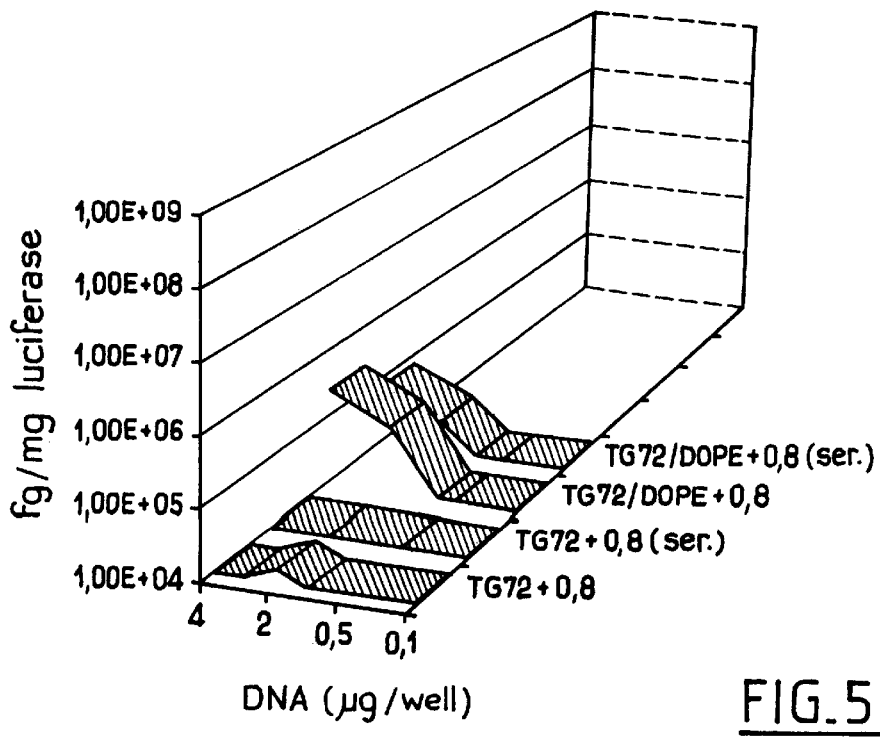
Figure 5C:
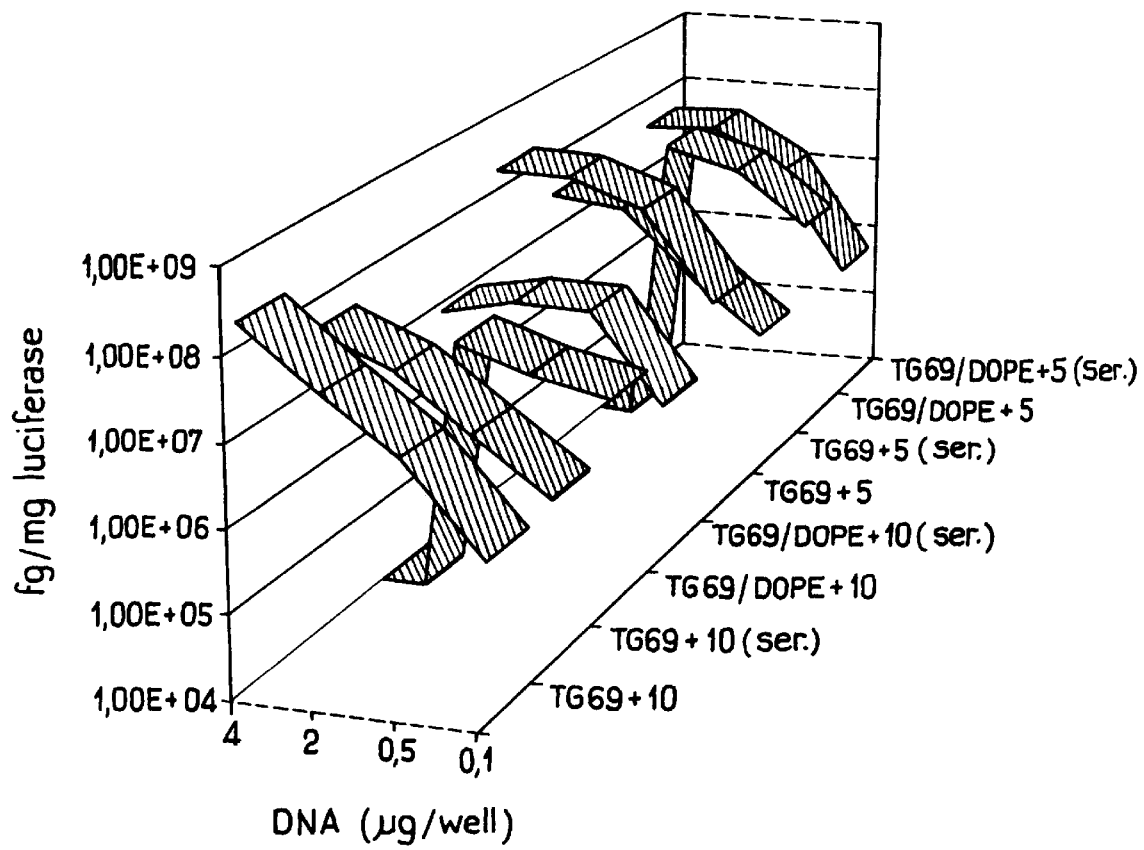

The efficacy of the complexes formed according to the preceding method described with the fluorinated compounds (see Example N) was studied on a culture of A549 cells according to the technique described in Example I. The charge ratios tested are chosen among the ratios 10, 5, 2.5, 1.25 and 0.8 (see FIGS. 5 A to G). The tests were also carried out in the absence or in the presence (indicated in the figures by ser.) of serum or of DOPE, and for various quantities of DNA (0.1, 0.5, 2 or 4 µg). The results (FIGS. 5 A to G) show that:

pcTG69 (FIG. 5C) makes it possible to observe, under the conditions tested, luciferase expression levels comparable to those obtained with nonfluorinated analogous C14 or C16 compounds. Moreover, other results, not shown in FIG. 5, showed that the best results were obtained with pcTG69 with a charge ratio of 2.5, in the presence or in the absence of DOPE or of serum, pcTG72 (FIGS. 5A and B) makes it possible to obtain satisfactory transfection rates for a charge ratio of 10, in the presence or in the absence of DOPE or of serum; on the other hand, for a charge ratio of 1.25 or 0.8, it is observed that the presence of DOPE is a factor which makes it possible to enhance the transfection rate, in particular in the presence of quantities of DNA greater than 0.1 μg, pcTG71 (FIGS. 5D and E) allow suitable transfection rates to be obtained only in the presence of DOPE, for charge ratios of 1.25, 0.8 or 10, in particular for quantities of DNA greater than 0.5 μg. Under the conditions tested, transfections in the presence of DOPE do not appear to be affected by the presence of serum in the medium, pcTG70 (FIGS. 5F and G): For charge ratios of 10 or 5, the transfection rates observed are effective, in the presence or in the absence of DOPE or of serum. On the other hand, for lower charge ratios (1.25 or 0.8), the presence of DOPE appears to be required.

What is claimed is:

1. A complex comprising
(i) at least one compound of formula I:

$$\begin{array}{l} CH_2-O-R_1 \\ CH-O-R_2 \\ CH_2-X-\underset{\|}{C}-CH_2-(N-(CH_2)_{\overline{m}})_{\overline{n}}NH_2 \\ \phantom{CH_2-X-}O \phantom{-CH_2-}H \end{array}$$

in which:
$R_1$ and $R_2$, which are identical or different, are $C_6$–$C_{23}$ alkyl or alkenyl radicals which are linear or branched, or radicals —C(=O)-($C_6$–$C_{23}$) alkyl or —C(=O)-($C_6$–$C_{23}$) alkenyl which are linear or branched, X is an oxygen atom or an amino radical —$NR_3$, $R_3$ being a hydrogen atom or an alkyl radical having 1 to 4 carbon atoms, n is a positive integer from 1 to 6, m is a positive integer from 1 to 6, and when n>1, m may be identical or different, wherein said compound is in a cationic form, and (ii) at least one active substance comprising at least one negative charge.

2. The complex of claim 1, wherein $R_1$ and $R_2$, which are identical or different, are linear —C(=O) alkyl or linear —C(=O) alkenyl radicals.

3. The complex of claim 1, wherein $R_1$ and $R_2$, which are identical or different, are —C(=O) alkyl or —C(=O) alkenyl radicals comprising from 12 to 20 carbon atoms.

4. The complex of claim 1, wherein n is an integer chosen from the numbers 2, 3 or 4.

5. The complex of claim 1, wherein m is an integer chosen from the numbers 2, 3 or 4.

6. The complex of claim 1, wherein $R_1$, $R_2$ or a combination thereof is fluorinated.

7. The complex of claim 6, wherein the number of fluorinated carbon atoms on $R_1$, $R_2$ or a combination thereof may range from 1 to 12.

8. The complex of claim 6, wherein $R_1$, $R_2$ or a combination thereof are alkyl radicals having 15 carbons and the number of fluorinated carbon atoms on the chains $R_1$, $R_2$ or a combination thereof is 4.

9. The complex of claim 1, wherein the N—H and $NH_2$ groups are substituted with methyl or ethyl radicals instead of hydrogen.

10. The complex of claim 1, wherein said compound comprises from 2 to 7 positive charges.

11. The complex of claim 1, wherein said compound has a formula selected from the group consisting of:

Formula II $C_{13}H_{27}$ ...

wherein n = 2 [pcTG18 or n = 3 [pcTG33 II];

Formula III $C_{15}H_{31}$ ...

wherein n = 2 [pcTG21 or n = 3 [pcTG34 III];

Formula IV $C_{17}H_{35}$ ...

wherein n = 2 [pcTG19] or n = 3 [pcTG36 IV];

Formula V $C_{17}H_{33}$ ...

wherein n = 2 [pcTG20 or] n = 3 [pcTG35] or n = 4 [pcTG56 V]; or

Formula VI
C18:1, [cis]-9

$C_{17}H_{35}$ ...

n = 2 [pcTG22] or n = 4 [pcTG90 VI].

12. The complex of claim 1, further comprising at least one adjuvant which enhances the formation of the complex between said compound and said active substance.

13. The complex of claim 12, wherein said adjuvant is a neutral or zwitterionic lipid.

14. The complex of claim 13, wherein said neutral or zwitterionic lipid is or is derived from a triglyceride, a diglyceride, cholesterol, a phosphatidylethanolamine (PE), phosphatidylcholine, phosphocholine, sphygomyelin, ceramide or cerebroside.

15. The complex of claim 14, wherein said neutral or zwitterionic lipid is dioleylphosphatidylethanolamine (DOPE).

16. The complex of claim 14, wherein the compound/adjuvant weight ratio is between 0.1 and 10.

17. The complex of claim 1, wherein said active substance is a nucleic acid comprising a cDNA, a genomic DNA, a plasmid DNA, an antisense polynucleotide, a messenger RNA, a ribosomal RNA, a ribozyme, a transfer RNA, or a DNA encoding such RNAs.

18. The complex of claim 1, wherein said complex has a size of less than 500 nm.

19. The complex of claim 1, wherein said complex has a size of less than 100 nm.

20. The complex of claim 1, wherein a ratio between positive charges of said cationic compound(s) and negative charges of said active substance ranges from 0.05 to 20.

21. A composition comprising an effective amount of the complex of claim 1 and a pharmaceutically acceptable carrier therefor.

22. The composition of claim 21, further comprising at least one adjuvant which enhances the transfective power of said complex.

23. The composition of claim 21, wherein said adjuvant comprises chloroquine, a protic polar compound selected from the group consisting of propylene glycol, polyethylene glycol, glycerol, ethanol, 1-methyl-L-2-pyrrolidone and a derivative thereof, or an aprotic polar compound selected from the group consisting of dimethyl sulfoxide (DMSO), diethyl sulfoxide, di-n-propyl sulfoxide, dimethyl sulfone, sulfolane, dimethylformamide, dimethylacetamide, tetramethylurea, acetonitrile and a derivative thereof.

24. A method of delivery comprising transferring at least one therapeutically active substance into target cells along with an effective amount of the compound of claim 1.

25. The method of claim 24, wherein said target cell is a mammalian cell.

26. The method of claim 25, wherein said target cell is selected from a muscle cell, a hematopoietic stem cell, or a cell of the airways.

27. The method of claim 26, wherein said cell of the airways is selected from a tracheal or pulmonary cell.

28. A method of delivery of therapeutically active substances in the human or animal body, said method comprising administering the complex of claim 1 to a human or animal in need of such prevention or treatment.

29. The method of claim 27, wherein said complex is administered by intramuscular injection, by inhalation, by intratracheal injection, by instillation, by aerosolization, by the topical route or by the oral route.

30. The complex of claim 1, wherein said compound is conjugated with one or more targeting components via at least one carbon atom from those present in groups $R_1$, $R_2$, or $R_3$.

31. The complex of claim 1, wherein said compound is conjugated with one or more targeting components via at least one secondary or primary nitrogen atom.

\* \* \* \* \*

UNITED STATES PATENT AND TRADEMARK OFFICE
CERTIFICATE OF CORRECTION

PATENT NO. : 6,218,370 B1
DATED : April 17, 2001
INVENTOR(S) : Rainer Bischoff et al.

It is certified that error appears in the above-identified patent and that said Letters Patent is hereby corrected as shown below:

Please replace the paragraph beginning on column 5, line 36 and ending on column 6, line 35 with the following:

-- According to a preferred embodiment of the invention, said compound is chosen from the group consisting of the following formulae:

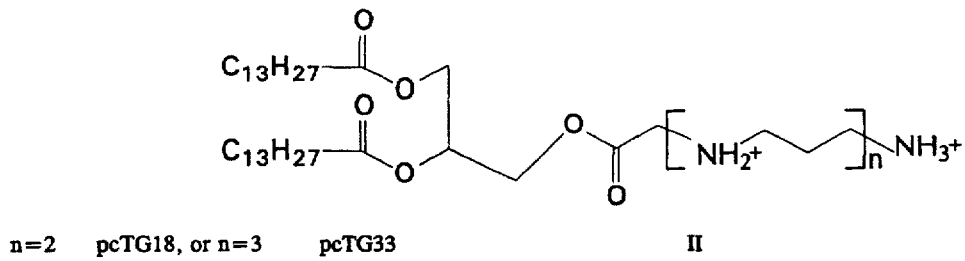

n=2    pcTG18, or n=3    pcTG33                II

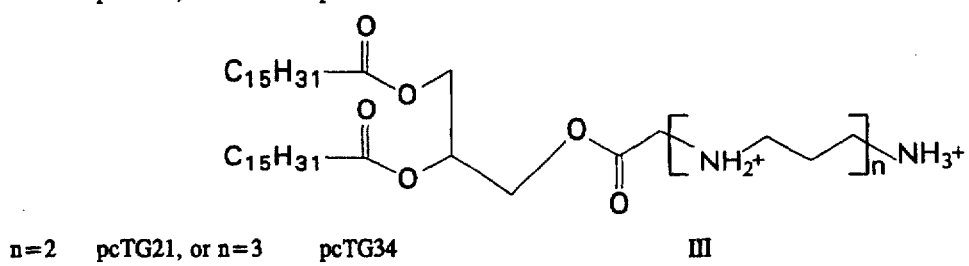

n=2    pcTG21, or n=3    pcTG34                III

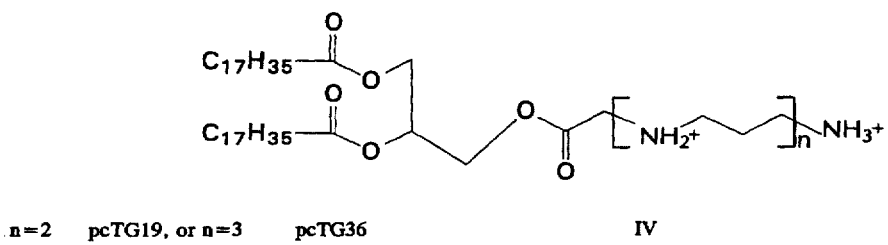

n=2    pcTG19, or n=3    pcTG36                IV

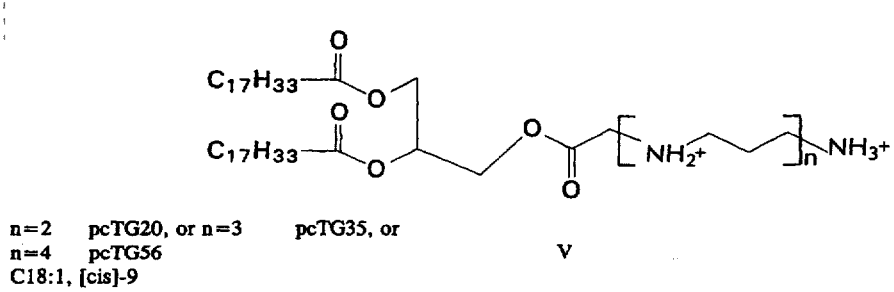

n=2    pcTG20, or n=3    pcTG35, or
n=4    pcTG56                                  V
C18:1, [cis]-9

UNITED STATES PATENT AND TRADEMARK OFFICE
CERTIFICATE OF CORRECTION

PATENT NO. : 6,218,370 B1
DATED : April 17, 2001
INVENTOR(S) : Rainer Bischoff et al.

It is certified that error appears in the above-identified patent and that said Letters Patent is hereby corrected as shown below:

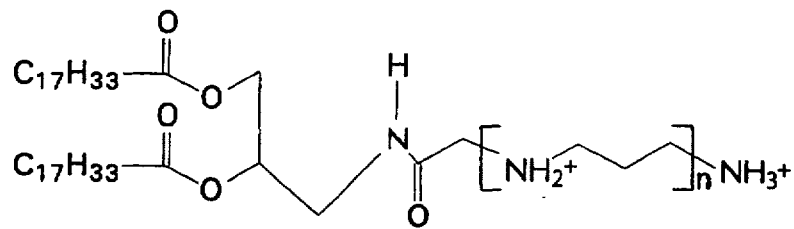

n=2   pcTG22, or   n=4   pcTG90                              VI.--

Claims,
Kindly replace claim 11 as follows:
11. The complex of claim 1, wherein said compound has a formula selected from the group consisting of:

Formula II

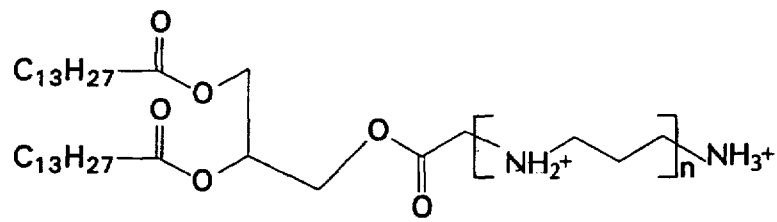

wherein n=2 or n=3;

UNITED STATES PATENT AND TRADEMARK OFFICE
CERTIFICATE OF CORRECTION

PATENT NO. : 6,218,370 B1
DATED : April 17, 2001
INVENTOR(S) : Rainer Bischoff et al.

It is certified that error appears in the above-identified patent and that said Letters Patent is hereby corrected as shown below:

Formula III

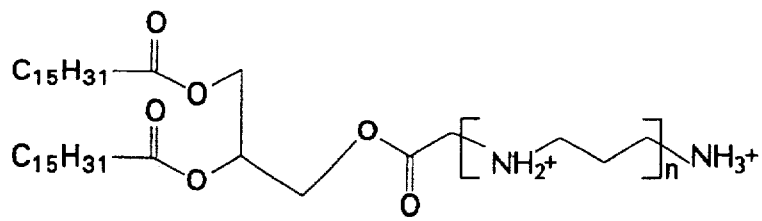

wherein n=2 or n=3;

Formula IV

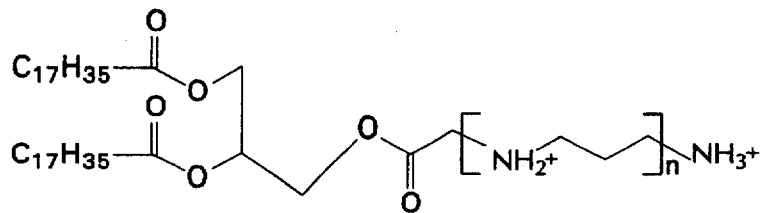

wherein n=2 or n=3;

UNITED STATES PATENT AND TRADEMARK OFFICE
CERTIFICATE OF CORRECTION

PATENT NO. : 6,218,370 B1
DATED : April 17, 2001
INVENTOR(S) : Rainer Bischoff et al.

It is certified that error appears in the above-identified patent and that said Letters Patent is hereby corrected as shown below:

Formula V

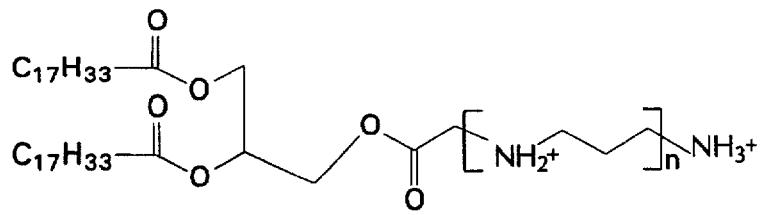

wherein n=2, n=3 or n=4; or

Formula VI

C18:1, [cis]-9

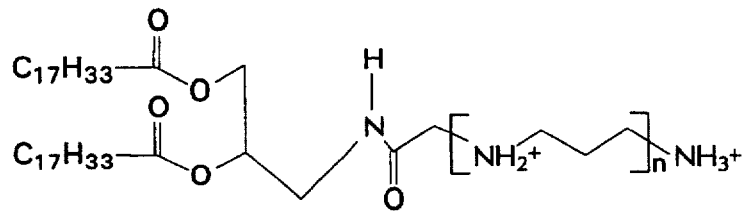

n=2 or n=4.

Signed and Sealed this

Twenty-third Day of April, 2002

Attest:

*Attesting Officer*

JAMES E. ROGAN
*Director of the United States Patent and Trademark Office*